United States Patent
Takeda et al.

(10) Patent No.: US 7,423,746 B2
(45) Date of Patent: Sep. 9, 2008

(54) CIRCUIT-PATTERN INSPECTING APPARATUS AND METHOD

(75) Inventors: Masayoshi Takeda, Tendo (JP); Hirokazu Ito, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/698,985

(22) Filed: Jan. 29, 2007

(65) Prior Publication Data
US 2007/0201018 A1 Aug. 30, 2007

(30) Foreign Application Priority Data
Feb. 28, 2006 (JP) .............................. 2006-053520

(51) Int. Cl.
*G01N 21/00* (2006.01)
(52) U.S. Cl. .............. 356/237.4; 356/237.2; 356/237.6; 250/306; 250/310
(58) Field of Classification Search ... 356/237.2–237.6; 250/306–310
See application file for complete search history.

(56) References Cited

U.S. PATENT DOCUMENTS

| 5,502,306 | A | 3/1996 | Meisburger et al. |
| 6,421,122 | B2 * | 7/2002 | Nara et al. ................. 356/394 |
| 2006/0133661 | A1 | 6/2006 | Takeda et al. |

FOREIGN PATENT DOCUMENTS

| JP | 59-160948 | 9/1984 |
| JP | 5-258703 | 10/1993 |
| JP | 2006-170907 | 6/2006 |

* cited by examiner

*Primary Examiner*—L. G. Lauchman
*Assistant Examiner*—Iyabo S Alli
(74) *Attorney, Agent, or Firm*—McDermott Will & Emery LLP

(57) ABSTRACT

A circuit pattern inspection apparatus and inspection method facilitate the creation of a recipe and the confirmation of a defect. The apparatus and method employ a dialogue-based operation for the creation of a recipe and the confirmation of a defect. Input items (such as contrast, calibration, etc.) for the recipe creation and their purposes are clarified. Input items (such as clustering, filtering, etc.) for the defect confirmation and their purposes are also clarified. The results obtained on the basis of these inputs are registered in the recipe.

5 Claims, 17 Drawing Sheets

MAP RENDERING MODE (1) MODE FOR DISPLAYING THE ENTIRE WAFER
(2) MODE FOR SUPERPOSING ONE OR MORE DIES OF WAFER
(3) MODE FOR SUPERPOSING ONE OR MORE SHOTS OF WAFER

MAP OPERATION MODE (1) OPERATION FOR SELECTING AN ARBITRARY DEFECT IN MAP
(2) OPERATION FOR SELECTING DEFECTS IN AN ARBITRARY AREA IN MAP
(3) OPERATION FOR ENLARGING/REDUCING THE SIZE OF AN ARBITRARY AREA IN MAP

FIG. 13

DISPLAY CONDITION DIALOG

200

| Valid | Filter item | Minimum value | Maximum value |
|---|---|---|---|
| ☐ | Defect coordinates | 0.0 | 99999.9 |
| ☐ | Defect die address | 0 | 99 |
| ■ | Defect area | 0.00000 | 999.99999 |
| ☐ | Defect size | 0.0 | 99999.9 |
| ☐ | Aspect ratio | 0.00 | 99.99 |
| ☐ | Classification code | 0 | 255 |
| ☐ | Cluster number | 0 | 999999 |
| ■ | Grayscale difference | -999 | 999 |

| Valid | Filter item | | |
|---|---|---|---|
| ☐ | Radius | | mm ▶ |
| ■ | Inspection method | Cell inspection | |
| ☐ | Number selected | | |

| Clustering method | Intra-die merge distance |
|---|---|
| Intra-die merge distance | 50.0 ▶ μm |
| Minimum number of elements | 10 |

Number of cluster groups  18

[Enter]  [Cancel]  [Close]

CIRCUIT-PATTERN INSPECTING APPARATUS AND METHOD

BACKGROUND OF THE INVENTION

1. Field of the Invention

The present invention relates to technologies for inspecting fine circuit patterns for semiconductor devices or LCDs on a substrate, particularly such circuit patterns on a semiconductor wafer. More specifically, the invention relates to such inspecting technologies whereby the circuit patterns formed on a semiconductor wafer are irradiated with light, laser light, or a charged-particle beam to obtain an exterior image of the wafer.

2. Background Art

Semiconductor devices are typically manufactured by repeating the steps of forming a circuit pattern on a semiconductor wafer using a photomask and then transferring the pattern on the semiconductor wafer by lithography and etching. During the manufacture of semiconductor devices, the quality of individual processes including the aforementioned lithography and etching processes, as well as the presence of foreign matter during the manufacturing steps, have a significant influence on the yield or the like of the final semiconductor device products. For this reason, it is important in the manufacture of semiconductor devices to detect or prevent abnormality in each step or the development of defects as early as possible. Thus, during the manufacture of semiconductor devices, the circuit pattern formed on the semiconductor wafer is inspected in each manufacturing step.

Various inspection apparatuses are used during the manufacture of semiconductor devices. One example is an optical exterior inspection apparatus that determines the presence of abnormality using an optical image obtained by irradiating the pattern with laser light or the like. Another example is an electron beam inspection apparatus whereby the pattern is scanned with a charged-particle beam, such as an electron beam, to acquire an image based on the intensity of signals of the secondary electrons or reflected electrons that are produced, wherein the presence of abnormality is determined using such image. Such various inspection apparatuses are actually being used for the inspection of circuit patterns.

Patent Document 1: JP Patent Publication (Kokai) No. 5-258703 A (1993)
Patent Document 2: U.S. Pat. No. 5,502,306
Patent Document 3: JP Patent Publication (Kokai) No. 59-160948 A (1984)

SUMMARY OF THE INVENTION

In the aforementioned types of inspection apparatuses, where the presence of abnormalities or defects in the circuit pattern formed on the semiconductor wafer is determined using an exterior image of the semiconductor wafer substrate surface that is obtained by light, laser light, or charged-particle beam irradiation, various inspection conditions need to be set in the apparatus in advance. These inspection conditions include, for example, a condition relating to the irradiation of the semiconductor wafer with light, laser light, or a charged-particle beam; a condition relating to the brightness of an acquired image of the semiconductor wafer acquired on the basis of the output of a detector under a certain irradiation condition; and a threshold condition for having the apparatus recognize a predetermined image in the acquired image as a defect. Such inspection conditions, which are the major ones, have a great impact on the inspection result. In addition, the setting of the individual inspection conditions and the adjustment of one inspection condition relative to another are complicated and difficult. As a result, it has not necessarily been the case that any user who uses these types of inspection apparatus can easily and accurately acquire an exterior image of the semiconductor wafer substrate surface or make a decision as to the presence of abnormalities based on such exterior image. Thus, the apparatuses have not been very easy to operate. While such inspection apparatuses are equipped with a screen for displaying the inspection result, the screen during the inspection condition setting operation is merely used for listing the main inspection conditions that need to be set. Thus, the screen function has not been fully exploited for the purpose of easy and accurate setting or adjustment of inspection conditions.

The consequence has been that in order to accurately detect abnormalities or defects on the surface of semiconductor wafer substrate using the aforementioned types of inspection apparatus, it has been necessary to engage the service of an expert who can set the individual inspection conditions and adjust their combinations accurately.

It is therefore an object of the invention to provide a circuit pattern inspection apparatus and method whereby, instead of just listing the major inspection conditions, the user is asked to enter necessary inspection conditions successively in a dialog fashion. In this way, the purpose of entering each condition can be clarified, and it becomes possible for the user to detect any defects quickly and accurately even if the user is not a semiconductor inspection expert.

In order to overcome the aforementioned problems, in one aspect, the invention provides a circuit pattern inspection apparatus which comprises:

an irradiation means for irradiating the surface of a substrate on which a wafer circuit pattern is formed with either light, laser light, or a charged-particle beam;

a detection means for detecting a signal produced by the substrate upon irradiation;

an inspection image acquisition means for acquiring an image of the wafer circuit pattern as an inspection image by converting the signal detected by the detection means into an image;

a defect determination means for comparing the inspection image obtained by the inspection image acquisition means with a reference image different from the inspection image that is acquired from an identical circuit pattern so as to determine a defect portion produced on the circuit pattern from which the inspection image has been acquired;

an analysis result display means for generating a defect confirmation screen on which an analysis image based on the inspection image acquired by the inspection image acquisition means and another analysis image based on the result of defect determination made by the defect determination means are arranged;

an input means for entering information on a defect confirmation screen generated by the analysis result display means in a dialog mode; and an image linkage means for changing, when an operation input has been made using the input means on either the analysis image based on the inspection image disposed or on the analysis image based on the result of determination that are arranged on the defect confirmation screen, the display contents of one analysis image are changed in a corresponding manner in operative linkage with the operation input made on the other analysis image via the input means.

In another aspect, the invention provides a circuit pattern inspection method which comprises the steps of:

irradiating the surface of a substrate on which a wafer circuit pattern is formed with light, laser light, or a charged-particle beam;

detecting a signal produced by the substrate upon irradiation;

imaging the thus detected signal and acquiring an image of the wafer circuit pattern as an inspection image;

comparing the inspection image with a reference image that is separated from the inspection image and that is acquired from an identical circuit pattern; and determining a defect portion produced on the circuit pattern from which the inspection image has been acquired, based on the result of comparison.

The method further comprises:

an analysis result display step of generating a defect confirmation screen on which an analysis image based on the inspection image and an analysis image based on the result of defect determination are arranged;

an input step of entering information on the defect confirmation screen generated in the analysis result display step in a dialog mode; and an image linkage step of changing, when an operation input has been made using the input means on either the analysis image based on the inspection image disposed or on the analysis image based on the result of determination that are arranged on the defect confirmation screen, the display contents of one analysis image are changed in a corresponding manner in operative linkage with the operation input made on the other analysis image via the input means.

The invention further provides a circuit pattern inspection apparatus which comprises means for allowing images of defects selected from a wafer map by dragging or by a chip to be viewed in a list.

The invention also provides a circuit pattern inspection apparatus capable of displaying detailed information about a defect selected, by dragging or by a chip, from a wafer map as one analysis image disposed on the defect confirmation screen, as another analysis image in a graph.

The invention also provides a circuit pattern inspection apparatus capable of setting at least a classification code and a clustering group from another analysis image, concerning a defect selected, by dragging or by a chip, from a wafer map as one analysis image disposed on the defect confirmation screen.

The invention further provides a circuit pattern inspection apparatus capable of creating filter information from a classification code and a clustering group that have been set from at least another analysis image, concerning a defect selected, by dragging or by a chip, from a wafer map as one analysis image disposed on the defect confirmation screen.

The invention further provides a circuit pattern inspection apparatus capable of registering the filter that has been created in a recipe.

Effects of the Invention

In accordance with the invention, the process of creating a recipe for an inspection apparatus can be greatly facilitated, thereby allowing a defect to be detected quickly and accurately.

BRIEF DESCRIPTION OF THE DRAWINGS

FIG. 13 shows a screen for the confirmation of the filtering information set state by the graph process processing unit.

DESCRIPTION OF THE PREFERRED EMBODIMENTS

In the following, preferred embodiments of the circuit pattern inspection apparatus and method according to the invention will be described with reference to the drawings.

By the way, the circuit pattern inspection apparatus and method are herein defined as inspection apparatus and method that enable the measurement of the dimensions, the observation, or the inspection of the exterior, of a substrate to be inspected, such as a semiconductor wafer on which a circuit pattern is formed, using light, laser light, or a charged-particle beam.

Figure 1:
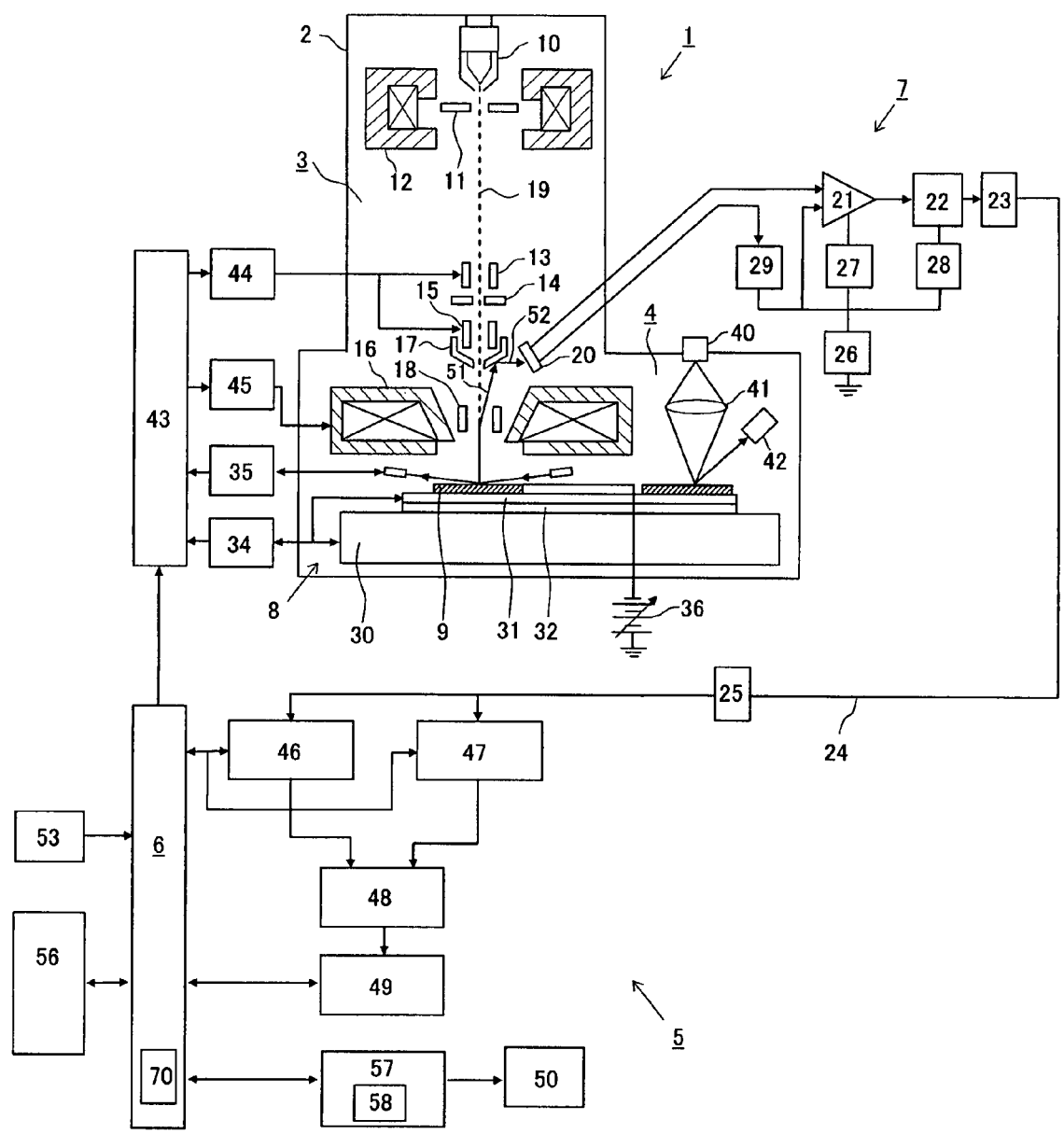
FIG. 1 shows a diagram of the circuit pattern inspection apparatus according to an embodiment of the invention.

FIG. 1 shows a block diagram of a circuit pattern inspection apparatus according to an embodiment of the invention.

Figure 2:
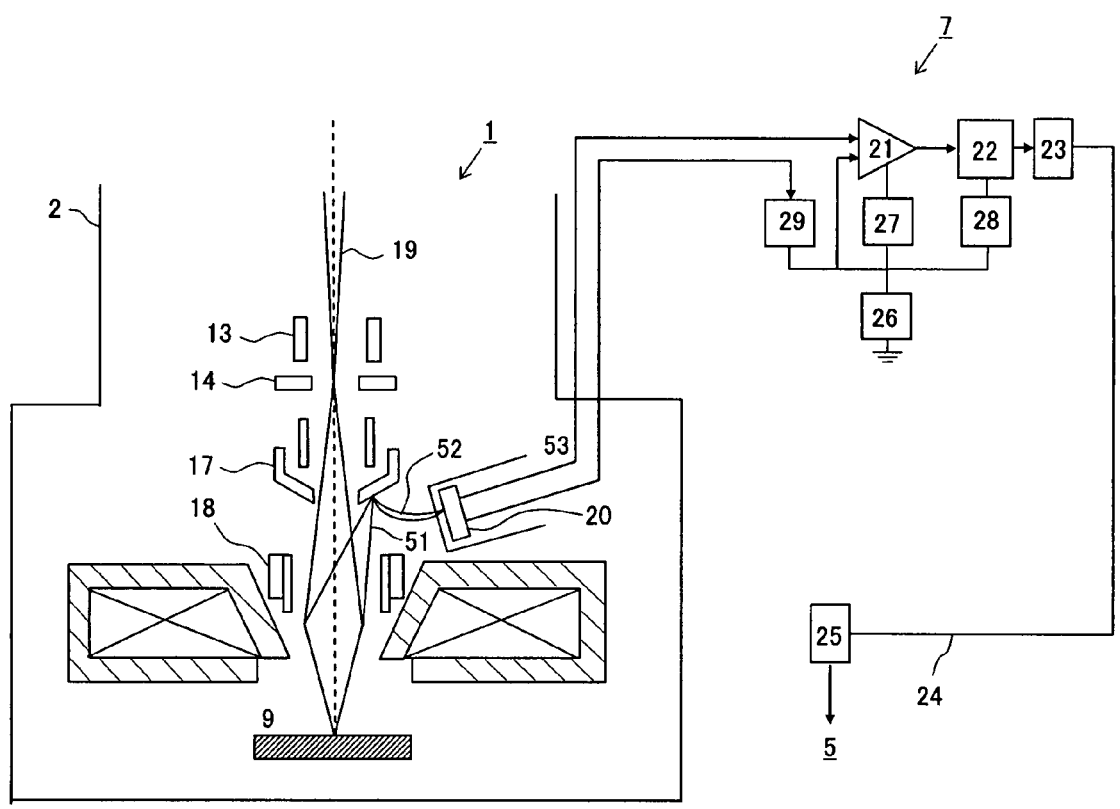
FIG. 2 shows a partially enlarged block diagram of the inspection apparatus of FIG. 1.

FIG. 2 shows a partially enlarged view of the inspection apparatus shown in FIG. 1.

The circuit pattern inspection apparatus 1 of the present embodiment is an example of the aforementioned inspection apparatus using a charged-particle beam.

Referring to FIG. 1, the circuit pattern inspection apparatus 1 includes an inspection chamber 2 that is evacuated, and a preliminary chamber (not shown) for transporting a substrate 9 to be inspected into the inspection chamber 2. The inspection chamber 2 and the preliminary chamber can be independently evacuated by evacuating means, which is not shown. In addition to the inspection chamber 2 and the preliminary chamber, the inspection apparatus 1 further includes an image processing unit 5 and a control unit 6. The inspection chamber 2 is fitted with an electro-optical system 3, a secondary electrons detection unit 7, a sample chamber 8, and an optical microscope unit 4.

The structure of the inspection chamber 2 is described below.

The electro-optical system 3 includes an electron gun 10, an electron beam extraction electrode 11, a condenser lens 12, a blanking deflector 13, an aperture 14, a scanning deflector 15, an objective lens 16, a reflecting plate 17, and an ExB deflector 18.

In the illustrated example, the electron gun 10 includes a thermal field transmission electron source of a diffusion supply type. This thermal field transmission electron source of a diffusion supply type can ensure stable electron beam current as compared with the conventional electron sources, such as a tungsten (W) filament electron source or a cold field emission electron source, thereby providing an electron beam image with little brightness fluctuations. Further, the electron source allows the electron beam current from the electron gun 10 to be set at a high value, so that high-speed inspection can be realized.

The electron beam with which the sample is irradiated (to be hereafter referred to as a primary electron beam) 19 is generated by the thermal field transmission electron source in the electron gun 10 and emitted therefrom upon application of an extraction voltage across the electron gun 10 and the extraction electrode 11. The primary electron beam 19 is accelerated by applying a high-voltage negative potential to the electron gun 10. As a result, the primary electron beam 19 travels in the direction of a sample base 30 with an amount of energy corresponding to the applied potential. After being converged by the condenser lens 12, the beam passes through the blanking deflector 13, the aperture 14, and the scanning deflector 15. The beam is further narrowed by the objective lens 16 and is then shone on the substrate 9 (which has a fine circuit pattern for a semiconductor wafer, chip, LCD, or a mask formed thereon) to be inspected, which is mounted on X-Y stages 31 and 32 on the sample base 30.

The blanking deflector 13 then deflects the primary electron beam 19 whenever necessary to blank the primary electron beam 19 such that the primary electron beam 19 does not pass through the aperture 14. The scanning deflector 15 deflects the primary electron beam 19 based on a scan signal so as to scan the substrate 9 with the beam at irradiation positions.

To the blanking deflector 13 and the scanning deflector 15, a scan signal generator 44 for generating the scan signal and a blanking signal is connected. To the condenser lens 12 and the objective lens 16, a lens power supply 45 is connected individually.

The ExB deflector 18 is disposed above the substrate 9 mounted on the X-Y stages 31 and 32. The ExB deflector 18 deflects the secondary electrons 51 in a predetermined direction by applying a voltage and a magnetic field to secondary electrons 51 that are produced upon irradiation of the substrate 9 with the primary electron beam 19. The ExB deflector 18 is capable of adjusting the amount of deflection of the secondary electrons 51 depending on the magnitude of the voltage and magnetic field applied to the secondary electrons 51. The ExB deflector 18 is also capable of varying the amount of application of the voltage and the magnetic field in operative association with a negative voltage applied to the substrate 9 as a sample by a retarding power supply 36, which will be described later.

The secondary electrons 51 deflected by the ExB deflector 18 strike the reflecting plate 17 under predetermined conditions. The reflecting plate 17, which is conical in shape, is integral with shield piping of the scanning deflector 15 for the primary electron beam 19 with which the substrate 9 is irradiated. As the accelerated secondary electrons 51 strike the reflecting plate 17, the reflecting plate 17 produces second secondary electrons (to be hereinafter referred to as a secondary electron beam) 52 having an energy of several V to 50 eV.

The secondary electrons detection unit 7 includes a secondary electrons detector 20 disposed above the objective lens 16 within the inspection chamber 2 that is evacuated. Outside the inspection chamber 2, there are disposed a preamplifier 21, an AD converter 22, a photoconversion means 23, a light transmission means 24, an electric conversion means 25, a high-voltage power supply 26, a preamplifier drive power supply 27, an AD converter drive power supply 28, a reverse-bias power supply 29, and an inspection chamber 2. The secondary electrons detector 20, the preamplifier 21, the AD converter 22, the photoconversion means 23, the preamplifier drive power supply 27, and the AD converter drive power supply 28 are floated to a positive potential by the high-voltage power supply 26. The secondary electron beam 52 produced by the striking of the reflecting plate 17 with the secondary electrons 51 is guided to the secondary electrons detector 20 by a pulling electric field due to the floating potential.

The secondary electrons detector 20 detects the secondary electron beam 52, which is produced by the striking of the reflecting plate 17 with the accelerated secondary electrons 51, in association with the scanning timing of the primary electron beam 19 by the scanning deflector 15. The secondary electrons detector 20 outputs an analog detection signal, which is fed to the preamplifier 21 disposed outside the inspection chamber 2, amplified by the preamplifier 21, and then supplied to the AD converter 22.

The AD converter 22 converts the analog detection signal supplied from the secondary electrons detector 20 via the preamplifier 21 into a digital signal successively so as to generate an image signal consisting of digital data. Thus, the AD converter 22 generates an image signal after digitalizing the analog detection signal immediately after it is supplied from the secondary electrons detector 20. In this way, it becomes possible to obtain an image signal having a higher SN ratio faster. The digital image signal outputted by the AD converter 22 is converted into an optical signal by the photoconversion means 23 which is then transmitted to the image processing unit 5 by the light transmission means 24.

In the following, the structure of the sample chamber 8 is described. In the case of the illustrated example, the sample chamber 8 includes a sample base 30, an X stage 31, a Y stage 32, a position monitoring length meter 34, and a device 35 for measuring the height of the substrate to be inspected.

On the X-Y stages 31 and 32, the substrate 9 to be inspected is mounted as a sample. During the inspection, it is possible to select either an inspection method whereby the primary electron beam 19 is moved in a scanning motion two-dimensionally while the X-Y stages 31 and 32 is kept stationery, or another inspection method whereby the primary electron beam 19 is moved in a scanning motion linearly along the X axis while the X-Y stages 31 and 32 are moved along the Y axis continuously at a constant speed. When inspecting a particular, relatively small region, the former method, i.e., the one whereby the primary electron beam 19, is moved in a scanning motion with the stage kept stationery, is more effective. The latter method, by which the primary electron beam 19 is moved in a scanning motion with the stage continuously moved at constant speed, is more effective when inspecting a relatively large region.

The position monitoring length meter 34, which comprises a length meter based on laser interference, for example, monitors the position of the X stage 31 and Y stage 32 in real-time. The monitoring result is transferred via a correction control circuit 43 to the control unit 6. Data about the number of rotations or the like of the individual motors for the X stage 31 and the Y stage 32 is also transferred from each driver to the control unit 6 via the correction control circuit 43. The control unit 6, as will be described later, can therefore accurately monitor the region or position that is irradiated with the primary electron beam 19 based on such data. The position error regarding the primary electron beam irradiated position can be corrected as needed in real-time by the correction control circuit 43 connected to the control unit 6. The region irradiated with the electron beam 19 can also be stored for each substrate 9 to be inspected.

The inspected substrate height measuring device 35 comprises an optical measuring device adapted for measurement that involves no electron beam, such as a laser interference measuring device or a reflected-light measuring device that measures a change based on the position of reflected light, for example. Using the height measuring device 35, the height of the substrate 9 mounted on the X-Y stages 31 and 32 is measured in real-time. In the illustrated example, the inspected substrate height measuring device 35 irradiates the substrate 9 with a thin beam of white light that has passed through a slit via a transparent window, detects the position of the reflected light with a position detection monitor, and then calculates the amount of change in the height based on the variation of the position. Measurement data is supplied from the inspected substrate height measuring device 35 to the correction control circuit 43. In the correction control circuit 43, based on the measurement data, the focal length of the objective lens 16 for narrowing the primary electron beam 19 is dynamically corrected, so that the primary electron beam 19 is constantly focused on the inspected region as it is irradiated. Alternatively, the warping or height distortion in the inspected substrate 9 may be measured prior to electron beam measurement, and then correction conditions can be set for each inspection region of the objective lens 16 based on such data.

The X-Y stages 31 and 32 are also adapted such that a negative voltage can be applied to the mounted substrate 9 from a retarding power supply 36. By adjusting the voltage of the retarding power supply 36, it becomes possible to decelerate the primary electron beam 19 and adjust the amount of electron beam irradiation energy delivered to the inspected substrate 9 to an optimum value without changing the potential of the electron gun 10. The secondary electrons 51 produced by the irradiation of the inspected substrate 9 with the primary electron beam 19 are accelerated by the negative voltage applied to the inspected substrate 9.

Hereafter, the structure of the optical microscope unit 4 in the inspection apparatus 1 is described.

The optical microscope unit 4 comprises a light source 40, an optical lens 41, and a CCD camera 42. The unit is installed inside the inspection chamber 2 nearby and yet at such distance from the electro-optical system 3 that they do not influence each other. The distance between the electro-optical system 3 and the optical microscope unit 4 is a known, predetermined distance. The X stage 31 or the Y stage 32 travels the known distance between the electro-optical system 3 and the optical microscope unit 4 in a reciprocating manner, thus enabling the substrate 9 to be inspected by the electro-optical system 3 and the optical microscope unit 4 independently.

In the present embodiment, the digital image signal about the surface of the substrate 9 that has been imaged by the CCD camera 42 of the optical microscope unit 4 is also converted into an optical signal by the photoconversion means 23, as in the case of the digital image signal about the surface of the substrate 9 that is based on the detection signal from the aforementioned secondary electrons detector 20. The thus converted optical signal is then transmitted by the light transmission means 24 to the image processing unit 5.

In the following, the structure of the image processing unit 5 in the inspection apparatus 1 is described.

The image processing unit 5 comprises a first image storage unit 46, a second image storage unit 47, a computing unit 48, a defect determination unit 49, and a monitor 50.

The digitized electron beam image signal about the inspected substrate 9 that has been detected by the secondary electrons detector 20 provided in the inspection chamber 2 of the digitized the inspection apparatus 1, and the optical image signal about the inspected substrate 9 that has been imaged by the CCD camera 42 are, in the illustrated example, both converted into optical signals and then transmitted to the image processing unit 5 via the light transmission means 24.

These optical signals transmitted from the inspection chamber 2 corresponding to the electron beam image signal and the optical image signal about the inspected substrate 9, are converted back to electric signals by the electric conversion means 25 provided in the image processing unit 5. Thereafter, the electron beam image signal about the inspected substrate 9 is fed to the first image storage unit 46 or the second image storage unit 47 where it is stored under the control of the control unit 6.

The computing unit 48 carries out various kinds of image processing, such as: position alignment between the image signal stored in one storage unit 46 (47) and the image signal stored in the other storage unit 47 (46); normalization of signal levels; and elimination of noise signal. The computing unit 48 then carries out logical comparison between the both image signals.

The defect determination unit 49 compares the absolute value of a differential image signal computed by the computing unit 48 with a predetermined threshold value. If the differential image signal level is greater than the predetermined threshold value, the relevant pixels are determined to be defect candidates, and the position and the number of such defects are acquired.

The resultant information about the electron beam image or the optical image fed to the image processing unit 5, or the position or the number of defects, including the result of determination by the defect determination unit 49, is allocated a defect ID (Identification) by the control unit 6 as will be described later so as to identify each defect. The information is then bundled for each substrate 9 to be inspected and stored in the storage unit 56, which will be described later, as the defect inspection result data for the identification of each defect. The information is also displayed on the monitor 50 by way of the display control unit 57. In the present embodiment, the display control unit 57 includes an OSD (On Screen Display) means 58.

Hereafter, the structure of the control unit 6 in the inspection apparatus 1 is described.

The control unit 6 controls the individual units of the inspection apparatus 1 by supplying an operation control instruction to each unit of the apparatus. For this purpose, the apparatus is adapted to receive relevant instructions and operating conditions. In the present embodiment, the control unit 6 has connected thereto an input operating portion 53, such as a keyboard or a mouse, for setting and entering instructions and operating conditions, and a storage unit 56 for storing inspection results or recipes, which will be described later. The control unit 6 is further equipped with a condition setting/adjusting control means 70 for controlling the display of inspection results or GUI (Graphical User Interface) on the monitor 50, and controlling the operation of an OSD means 58 provided in the display control unit 57.

Based on the operation made via the input operating portion 53, various observation conditions can be set in the control unit 6 in advance, the conditions including the acceleration voltage upon generation of an electron beam, the deflection width of the electron beam, deflection rate, the signal acquisition timing in the secondary electrons detection device, and the sample base transfer rate, for example, either selectively or freely as required by a particular purpose.

The control unit 6 monitors position or height errors using the correction control circuit 43 based on the signals from the position monitoring length meter 34 and the inspected substrate height measuring device 35. Based on the result of such monitoring, the control unit 6 produces a correction signal and supplies it to the objective lens power supply 45 and the scan signal generator 44 so that the electron beam is shone at a correct position at all times.

The control unit 6, in order to acquire an image of the inspected substrate 9 using the electro-optical system 3, irradiates the inspected substrate 9 with a narrowed primary electron beam 19. As a result, secondary electrons 51 are caused, which are then detected in synchronism with the scanning motion of the primary electron beam 19 and the movement of the X-Y stages 31 and 32. An image signal indicating the surface of inspected substrate 9 is thereafter obtained from the AD converter 22 in the secondary electrons detection unit 7.

Furthermore, in the inspection apparatus 1 of the present embodiment, the control process for the setting and entry of inspection conditions necessary for the inspection of the inspected substrate 9 using the electro-optical system 3 is carried out by the condition setting/adjusting control means 70 or the like in the control unit 6. How the control process is performed by the condition setting/adjusting control means 70 will be described later.

In the inspection apparatus 1 having the above-described configuration, it is indispensable to increase the inspection speed for an automatic inspection of circuit patterns. Accordingly, the electro-optical system 3 does employ the slow-speed scanning of the electron beam using a pA-order electron beam current, or the superposition of individual scan images obtained by a number of scans, which are carried out by conventional SEMs (scanning electron microscopes). Further, in the inspection apparatus, in order to inhibit the charging of the insulating members, it is necessary to conduct the electron beam scan at high speed and only once or a few times. Thus, in the inspection apparatus 1 of the present embodiment, the electro-optical system 3 is constructed such that an image can be formed by just one scan of a large-current electron beam on the order of about 100 times or more of the current in conventional SEMs, such as 100 nA, for example. For this reason, the scan width is 100 μm, each pixel has an area of 0.1 μm$^2$, and each scan is conducted in 1 μs.

Hereafter, an example of the application of the foregoing circuit pattern inspection apparatus and method to the inspection of a semiconductor wafer is described.

Figure 3:
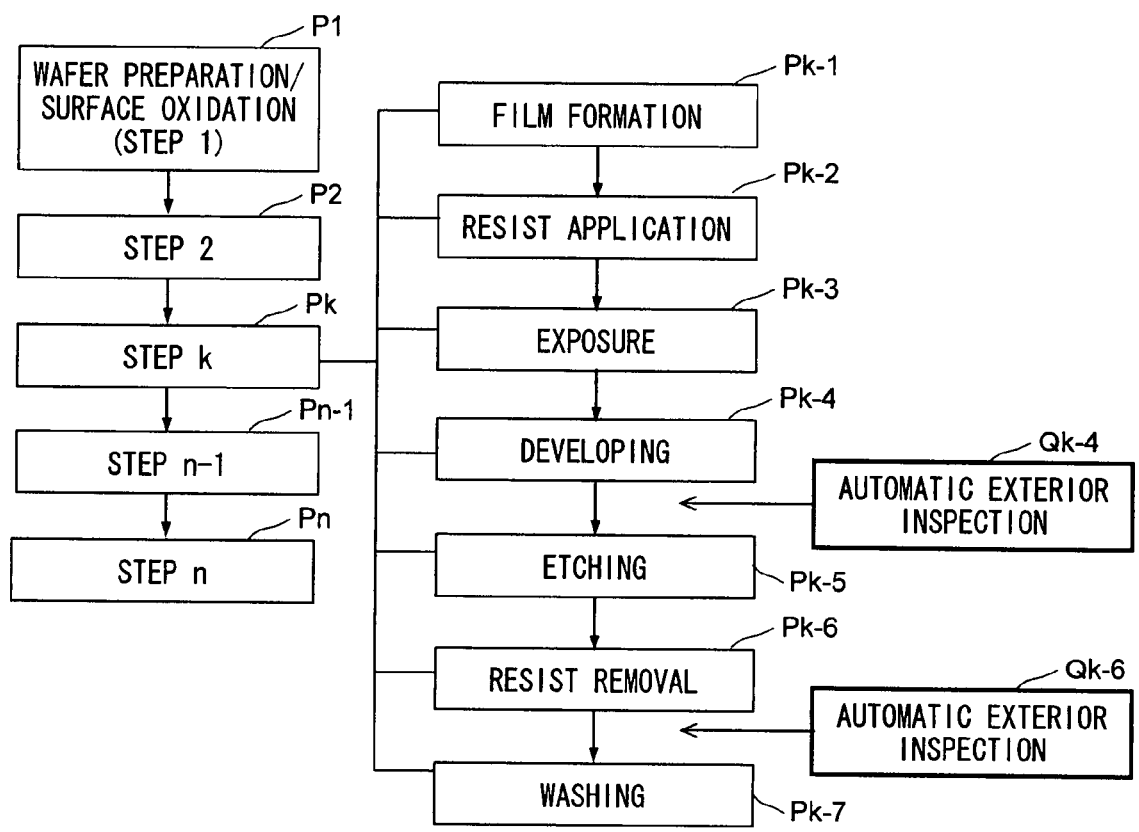
FIG. 3 shows a semiconductor device manufacturing process according to an embodiment of the invention.

FIG. 3 shows a diagram of a manufacturing process for a semiconductor device according to an embodiment.

As shown in FIG. 3, the semiconductor device is manufactured by repeating a number of pattern formation steps P1 to Pn. For example, a pattern formation step Pk (k being any integer from 1 to n) is roughly composed of individual steps for film formation Pk-1, application of photosensitive resist Pk-2, exposure Pk-3, developing Pk-4, etching Pk-5, resist removal Pk-6, and washing Pk-7.

In such semiconductor device manufacturing process, a circuit pattern for a semiconductor device cannot be formed normally on the substrate unless manufacturing process conditions are optimized in each of the steps Pk-1 to Pk-7.

For example, if an abnormality develops in the film formation step Pk-1 in FIG. 3, particles are produced and become attached to the semiconductor wafer surface, resulting in an isolated defect or the like. If the exposure conditions pertaining to the focal point or exposure time in the exposure apparatus are not optimized in the exposure step Pk-3, the amount or intensity of the light with which the resist is irradiated might be too much or too little at one location or another, resulting in a short circuit, disconnection, pattern thinning, etc. Also in the exposure step Pk-3, if there is a defect in the mask/reticle upon exposure, a similar pattern shape abnormality develops at the same location between shots, which are units of exposure. In the etching step Pk-5, short circuit, protrusions, an isolated defect, an opening defect or the like might develop if the etching amount is not optimized or due to a thin film or particles produced during etching. In the washing step Pk-7, if fine particles are produced by the reattachment of contaminant on the washing layer, peeled membrane, or other foreign matter, variation in the thickness of the oxide film tends to develop under certain drying conditions.

By applying the circuit pattern inspection method and apparatus 1 shown in FIG. 1 to a semiconductor device manufacturing process, development of abnormalities can be detected early and accurately, so that countermeasures can be taken in the relevant step and the processing conditions can be optimized so as to prevent the development of such defects.

For example, by implementing the circuit pattern inspection step Qk-4 after the developing step Pk-4, it can be presumed that the exposure or focusing conditions in the exposure apparatus are not optimized in the exposure step Pk-3 upon detection of a photoresist pattern defect or disconnection is detected. In this case, these conditions can be immediately rectified by adjusting the focusing conditions or the amount of exposure. Further, by investigating whether or not such defects are commonly occurring between individual shots by referring to a defect distribution, it becomes possible to presume a defect in the photomask/reticle used for pattern formation and inspect or replace the photomask/reticle at early stages. The same goes for the other steps; namely, by implementing the inspection step using the circuit pattern inspection apparatus and method according to the invention, various defects can be detected and the cause of any abnormalities in each manufacturing step can be estimated based on the nature of the detected defect.

Thus, by implementing the circuit pattern inspection apparatus 1 and method according to the present embodiment inline for a semiconductor device manufacturing process, variations in various manufacturing conditions and the development of abnormalities can be detected in the inspection step on a real-time basis, making it possible to prevent the development of a large number of defects. Further, the circuit pattern inspection apparatus 1 and method of the present embodiment enable the prediction of the overall yield of the semiconductor device based on the extent or frequency of defects, thus enhancing the productivity of the semiconductor device.

Figure 4:
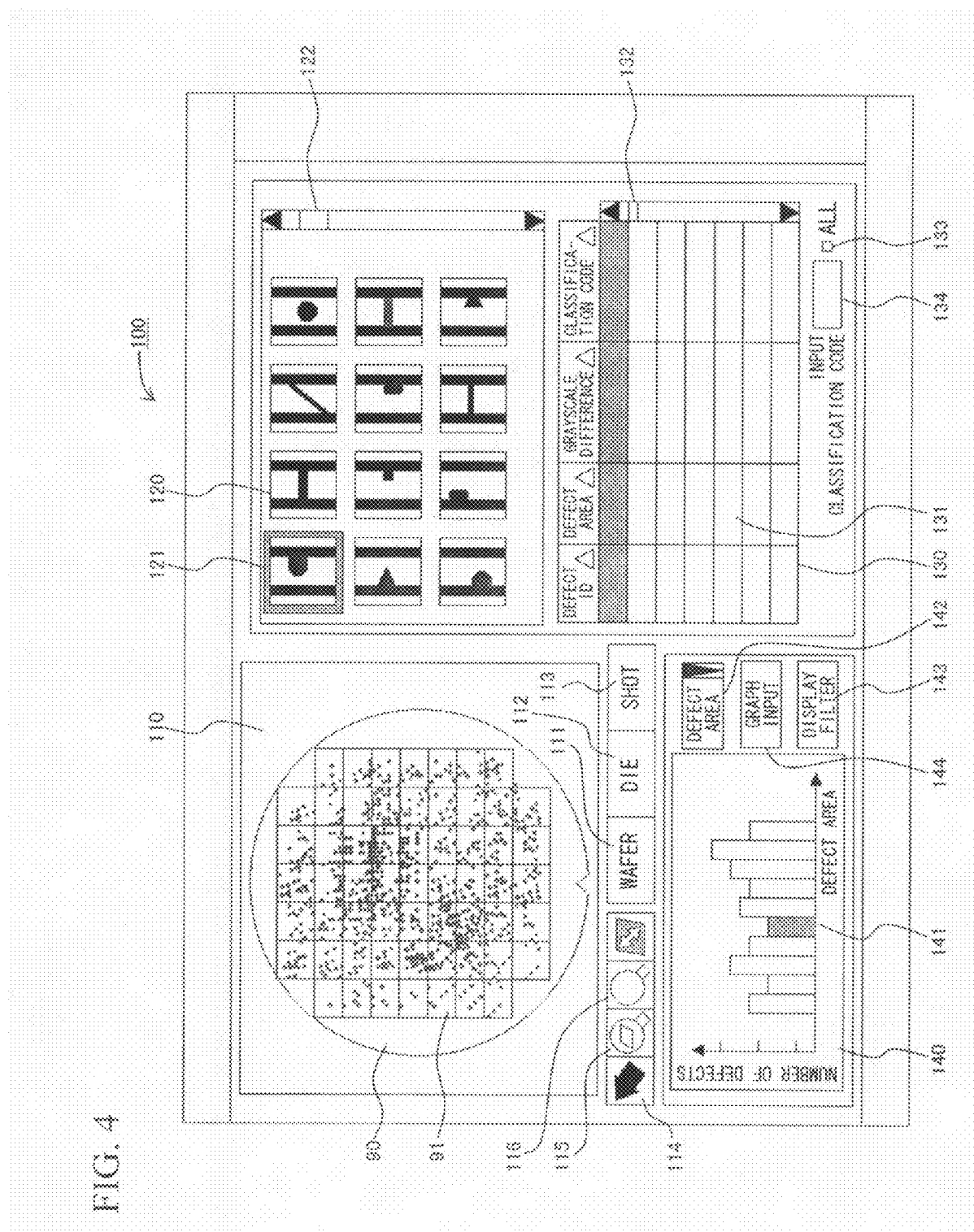
FIG. 4 shows a defect confirmation screen displayed on the monitor shown in FIG. 1 for the circuit pattern inspection apparatus and method of the present embodiment.

FIG. 4 shows a defect confirmation screen that is displayed on the monitor in accordance with the circuit pattern inspection apparatus and method of the present embodiment.

The defect confirmation screen 100 in accordance with the circuit pattern inspection apparatus and method in accordance with the present embodiment is composed of roughly four display areas; namely, a map display area 110, an image display area 120, a list display area 130, and a graph display area 140. This screen is displayed by the monitor 50 shown in FIG. 1.

On the defect confirmation screen 100 shown in FIG. 4, the map display area 110 shows a map Mp indicating the location of defects in a wafer 90 or a die 91. The image display area 120 shows images of defects selected from the map Mp displayed in the map display area 110. The list display area 130 shows a list of information about the corresponding defects selected from the map Mp. In the present embodiment, the list display area 130 is used for the setting of defect information. The graph display area 140 shows various kinds of detailed information about defects selected from the map Mp in a graph. It is used for the setting of inspection conditions or the like for defect determination in the present embodiment.

The defect confirmation screen 100, with these four display areas 110, 120, 130, and 140 enables quicker and easier defect confirmation and recipe creation through changes effected in association with user operations on the screen area of the individual monitor 50.

Hereafter, a recipe Rp required for the inspection of the wafer 90 is described.

In the circuit pattern inspection apparatus 1 of the present embodiment, the recipe Rp refers to a collection of data for the inspection of the wafer 90. In the present embodiment, the recipe Rp has a hierarchical structure consisting of variety data Dq and step data Dp. In the case of the circuit pattern inspection apparatus 1 of the present embodiment, recipes Rp are stored in the storage unit 56 shown in FIG. 1 in advance. A recipe Rp specified by the user is read each time the control unit 6 carries out an inspection operation, and necessary data, instructions based on the recipe Rp, or the like are supplied to the individual units of the inspection apparatus 1, such as the correction control circuit 43 and the defect determination unit 49.

Figure 5:
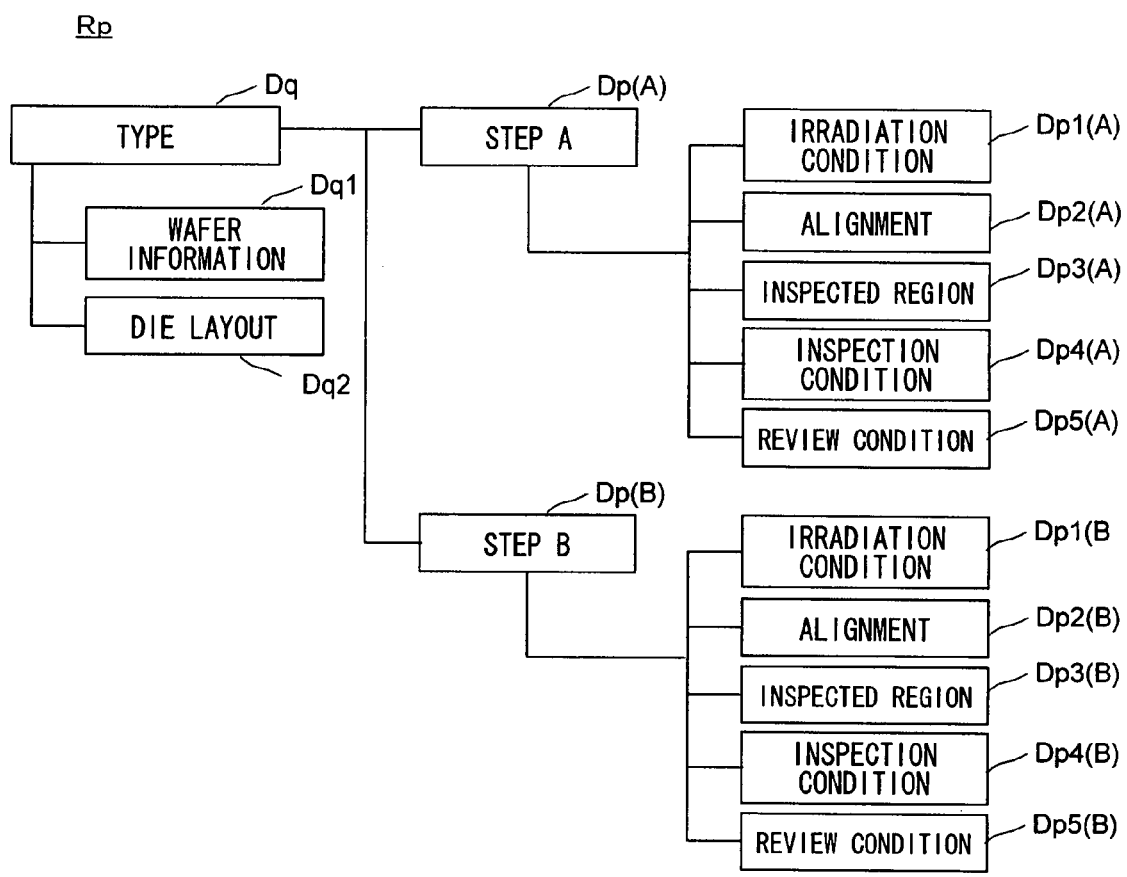
FIG. 5 shows a data block diagram of a recipe adopted in the circuit pattern inspection apparatus and method of the present embodiment.

FIG. 5 shows a data block diagram of a recipe adopted in the circuit pattern inspection apparatus and method in accordance with the present embodiment.

The variety data Dq in the recipe Rp indicates the type of circuit pattern to be inspected, such as a 64M-DRAM. In the present embodiment, the variety data Dq includes wafer information data Dq1 and die layout data Dq2.

In this case, the wafer information data Dq1 indicates the type of the wafer by the size of the wafer, such as in terms of the diameter of 200 mm or 300 mm, and by the wafer positioning method in terms of whether the wafer type is orientation flat or notch. The die layout data Dq2 indicates the size or number of shots, which are the units of wafer transcription, and the size or number of dies in a shot, for example.

The step data Dp in the recipe Rp indicates the type of operation step on the circuit pattern to be inspected, such as "LINE", which denotes wiring, for example. In the present embodiment, the step data Dp includes irradiation condition data Dp1, alignment data Dp2, inspection region data Dp3, inspection condition data Dp4, and review condition data Dp5.

In this case, the irradiation condition data Dp1 indicates the irradiation conditions of the charged-particle beam with which the wafer is irradiated, such as the retarding voltage for the charged-particle beam. During the inspection, the inspection apparatus 1 acquires an image by having the control circuit 6 set the voltage value using the correction control circuit 43. The alignment data Dp2 indicates data for correcting the misalignment of the wafer when it is conveyed from the preliminary chamber to the inspection chamber 2 (sample chamber). The data includes the die number, alignment coordinates within die layout, and die zero-offset data. The inspection region data Dp3 indicates the inspected region of the wafer. This region is managed in terms of the coordinates of the starting point and the end point of the region. The inspection condition data Dp4 indicates the type of image processing filter adapted for actual inspection, threshold values, the brightness of image, contrast, and so on. For example, the type of filter includes a smoothing filter for reducing noise in the image during inspection. The review condition data Dp5 indicates the conditions for the observation of the defects after inspection. The conditions include irradiation condition for observation purposes, cluster conditions, defect classification conditions, and filter conditions, for example.

In the present embodiment, the step data Dp is linked with another step data Dp via the variety data Dq. For example, when there are two kinds of step data Dp(A) and Dp(B) for step A and step B with respect to one variety data Dq, the step data Dp(B) for step B alone is read, and if the die layout data Dq2 for the variety data Dq associated with step B is changed, the die layout for the variety data Dq2 associated with step A is also changed. However, if the alignment data Dp2(B) for step B itself is rewritten (for example, if alignment die is changed), there is no influence on the alignment data Dp2(A) for step A.

In the inspection apparatus 1 of the present embodiment, by adopting such recipe structure, it becomes possible to make changes all at once in the same step.

Alternatively, if the recipe Rp data configuration shown in FIG. 5 is replaced with a structure such that a plurality of items of variety data Dq are adopted for each step data Dp, it is possible to provide step A and step B with wafer information and die layout information independently.

In the following, the data structure of the inspection result data Dr obtained as a result of an inspection of the wafer is described. The inspection result data Dr is stored in the storage unit 56 shown in FIG. 1 after inspection of the substrate 9 to be inspected (namely, after the inspection of the wafer 90), for each of the inspected substrates 9.

Figure 6:
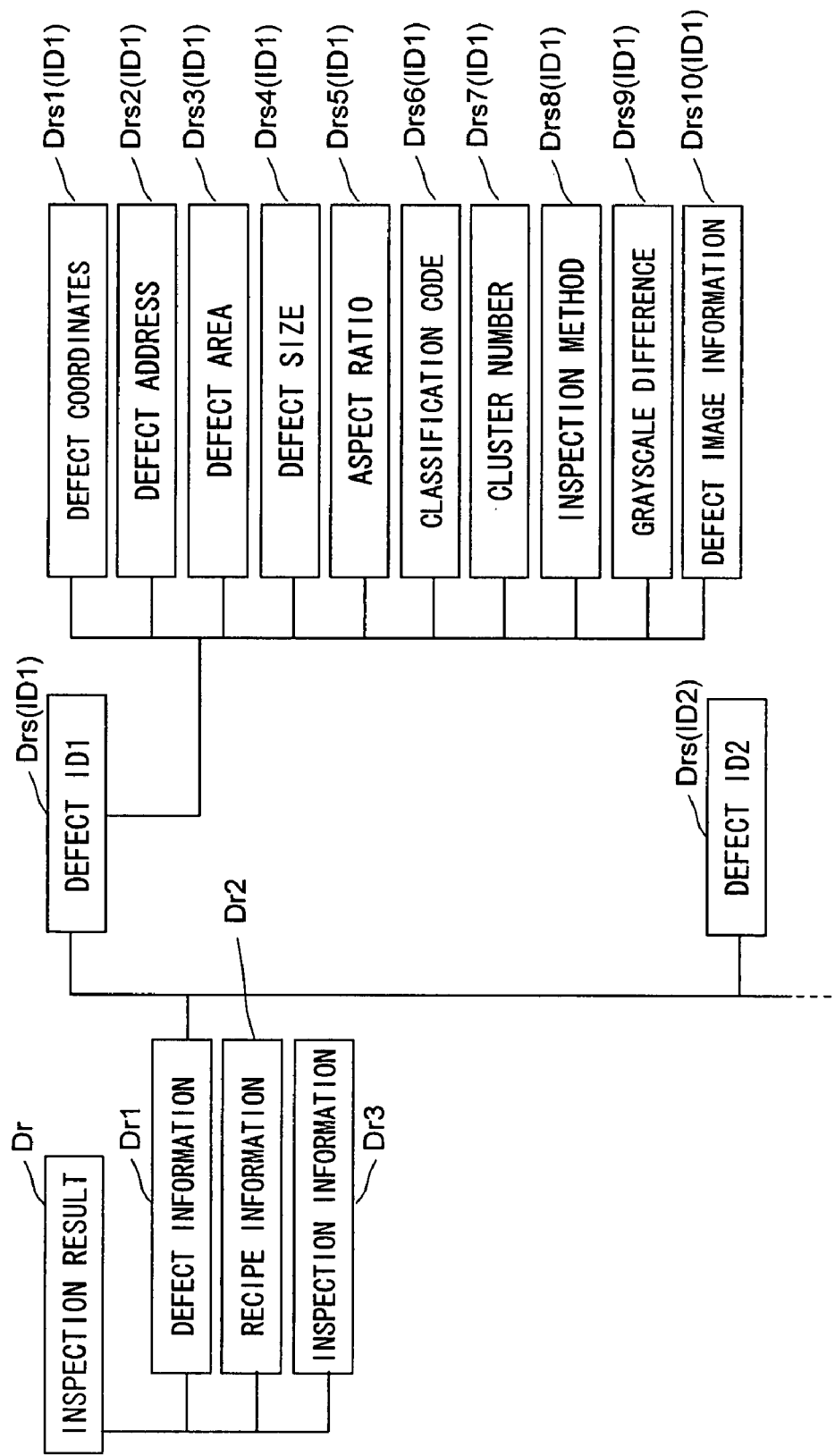
FIG. 6 shows a data block diagram of inspection result data in the circuit pattern inspection apparatus of the present embodiment.

FIG. 6 shows a data block diagram of inspection result data obtained by the circuit pattern inspection apparatus of the present embodiment.

In the present embodiment, the inspection result data Dr includes defect information data Dr1, recipe information data Dr2, and inspection information data Dr3, for example.

In the present case, the defect information data Dr1 indicates the information data concerning a defect detected by the image processing unit 5 in comparison with a reference image. The recipe information data Dr2 contains information about the recipe used during the inspection of a circuit pattern. For example, all of the data stored in the recipe Rp shown in FIG. 5 is stored. The inspection information data Dr3 indicates various data acquired upon detection of the aforementioned defect during the inspection of the wafer 90. For example, the data indicates the number of defects, the density of a defect relative to the area inspected, the time of inspection, and the date of inspection.

In the present embodiment, the defect information data Dr1 is associated with item information data Drs1 to Drsn for each defect site detected; namely, on defect ID data Drs basis. The item information data Drs1 to Drsn for each detected defect ID data Drs includes, in the present embodiment, defect coordinates data Drs1, defect address data Drs2, defect area data Drs3, defect size data Drs4, aspect ratio data Drs5, classification code data Drs6, cluster number data Drs7, inspection method data Drs8, grayscale difference data Drs9, and defect image information data Drs10, which are stored in association with the defect ID allocated for identifying each defect.

The defect coordinates data Drs1 indicates the position of a detected defect (coordinates position), and it includes three kinds of data; namely, stage coordinates, intra-die coordinates, and intra-shot coordinates. The defect address data Drs2 indicates the die address and shot address where the defect has been detected. The defect area data Drs3 indicates the area of the defect. The defect size data Drs4 indicates the size of the defect in the X and Y directions. The aspect ratio data Drs5 indicates the aspect ratio of the defect.

The classification code data Drs6 indicates the type of defect using two kinds of predetermined codes, depending on who gives the code. One is an automatic classification code by which the defects are classified by the inspection apparatus 1 itself shown in FIG. 1 according to a classification condition designated by the recipe. The other is a manual classification code by which the defects are classified according to a classification condition designated by the recipe based on the visual inspection of the defect image by the user. In the cluster number data Drs7, clustering numbers in accordance with the cluster condition designated in the recipe Rp are set.

The inspection method data Drs8 indicates the inspection method by which defect is detected. For example, the inspection method may be either cell comparison detection whereby a cell image to be inspected is compared with a predetermined reference cell image so as to detect a defect; die comparison detection whereby a die image to be inspected is compared with a predetermined reference die image; and mixed comparison detection whereby detection is made by both cell comparison and die comparison.

The grayscale difference data Drs9 indicates the difference in brightness between a defect portion and a reference portion. For example, the grayscale difference value becomes negative if the defect portion appears black relative to the reference portion on the image, and positive if the defect portion appears white. The defect image information in the image information data Drs10 indicates the image information that is linked with the defect image. For example, defect image address is set in the defect image information.

The inspection result data Dr with such data configuration is grouped for each of the substrates 9 inspected (namely, after the inspection of wafer 90), for example. The thus grouped inspection result data is then stored by the control unit 6 in the storage unit 56 based on the result of processing in each portion of the image processing unit 5 and is thus accumulated as inspection results.

In the following, the configuration of the defect confirmation screen 100 is described in greater detail, which screen is displayed by the monitor 50 based on the aforementioned inspection result data stored in the storage unit 56, under the control of the control unit 6 and by way of the display control unit 57.

The defect confirmation screen 100 shown in FIG. 4 is configured such that the map display area 110, the image display area 120, the list display area 130, and the graph display area 140 are linked with one another based on the information selected in each of the display areas 110, 120, 130, and.

Thus, in the present embodiment, in order to allow the user to control the setting and adjustment of various conditions in the recipe Rp necessary for inspection, the control unit 6 generates the defect confirmation screen 100 shown in FIG. 4 on which GUI buttons and the like are shown, with which the user can set or adjust the various conditions in the recipe Rp through a selection or entry operation.

For this purpose, the control unit 6, based on operations performed via the input operating portion 53 shown in FIG. 1 and the inspection result data shown in FIG. 6 that is stored and accumulated in the storage unit 56, controls the display of the GUI for the setting or adjustment of the inspection results and various conditions in the recipe. Thus, the control unit 6 also functions as a condition setting/adjusting control means 70 for controlling the operation of the OSD means 58 in the display control unit 57.

Figures 7, 8:
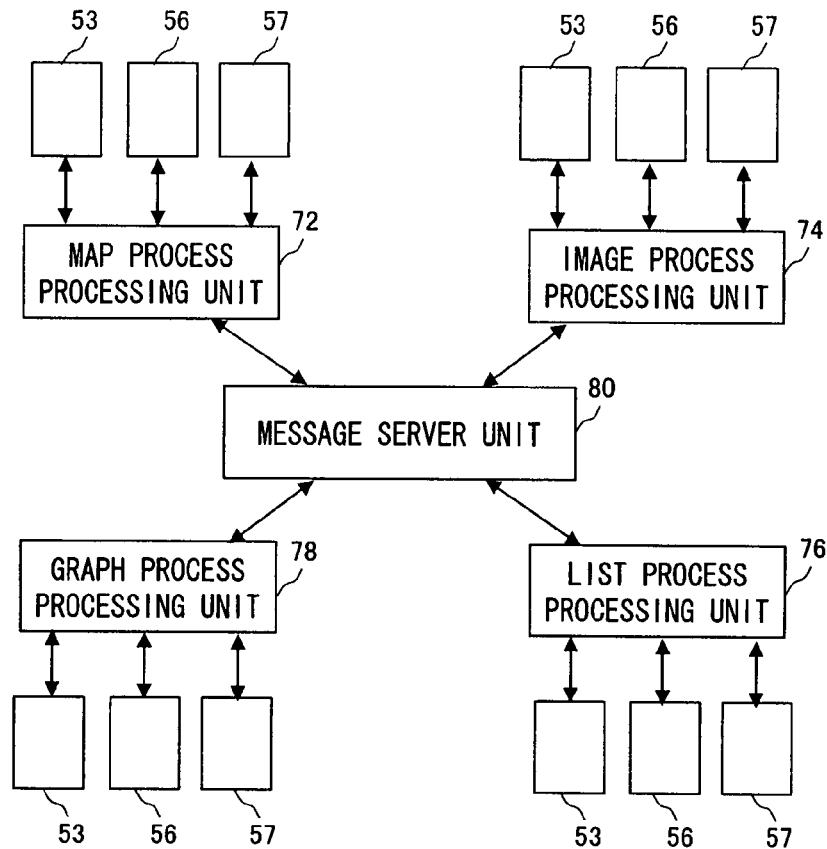
FIG. 7 shows an embodiment of a condition setting/adjusting control means provided in the control unit of the inspection apparatus of the present embodiment.
FIG. 8 shows different modes of display in the map display area produced by the map process processing unit.

FIG. 7 shows an example of the condition setting/adjusting control means provided in the control unit in the inspection apparatus of the present embodiment.

In the example shown in FIG. 7, the condition setting/adjusting control means 70 includes: a map process processing unit 72 for controlling the display of the screen in the map display area 110 of the defect confirmation screen 100 and the input of operations made by the user through the input operating portion 53 using the GUI buttons or the like; a image process processing unit 74 for similarly controlling the display of the screen in the image display area 120 and the input of operations made by the user through the input operating portion 53 using the GUI buttons or the like on the displayed screen; a list process processing unit 76 for similarly controlling the display of the screen in the list display area 130 and the input of operations made by the user through the input operating portion 53 using the GUI buttons or the like on the displayed screen; and a graph process processing unit 78 for similarly controlling the display of the screen in the graph display area 140 and the input of operations made by the user through the input operating portion 53 using the GUI buttons or the like on the displayed screen.

The individual process processing units 72 to 78 are configured in the same way as when they are individually connected to the input operating portion 53, the storage unit 56, and the display control unit 57 shown in FIG. 1. The process processing units 72 to 78 are capable of exchanging information and data via a message server portion 80 provided in the condition setting/adjusting control means 70 of the control unit 6, using broadcast or files. The process processing units 72 to 78 are configured to mainly control the display in the corresponding display areas 110 to 140 on the defect confirmation screen 100 and the input of operations made by the user through the input operating portion 53 using the GUI buttons or the like on the displayed screen.

In this case, the data connections between the individual process processing units 72 to 78 and the message server portion 80 are made via socket connection using a predetermined network address. Thus, the individual process processing units 72 to 78 have a connection structure in which they are aware of connection to the message server portion 80 alone and are not aware of the other process processing units 72 to 78.

Depending on the user setting in the process processing units 72 to 78 or the message server portion 80, some of the process processing units 72 to 78 may be specified not to be linked with each other. For example, the user might want to have all of the defects displayed on the display screen in the list display area 130 of the defect confirmation screen 100 by the list process processing unit 76. In that case, the linkage function of the list process processing unit 76 with respect to the other process processing units 72,74, and 78 may be turned off.

The screen size and position in the display areas 110 to 140 on the defect confirmation screen 100 displayed on the monitor 50 can also be freely changed by user settings. For example, in the present embodiment, the display size can be changed by dragging the frame line of the display area portion using the mouse in the input operating portion 53. The display position on the defect confirmation screen 100 can be changed by dragging the display area portion itself on the defect confirmation screen 100 of each of the process processing units 72 to 78. The settings concerning the size and position of display on the display areas 110 to 140 in each of the process processing units 72 to 78 are valid upon next startup, and they can be returned to default startup coordinates and size at any time. Thus, in the present embodiment, the screen size and position of in the display areas 110 to 140 can be freely changed, providing the user with an easy-to-use defect confirmation screen 100.

Hereafter, the display areas 110 to 140 generated by the corresponding process processing units 72 to 78 on the defect confirmation screen 100 are described in detail.

The map process processing unit 72, based on the defect information data Dr1 in one inspection result data Dr stored in the storage unit 56, and on the wafer information data Dq1 in the recipe Rp used for the inspection that is stored as the corresponding recipe information data Dr2, the map Mp for the entire wafer 90 is rendered in the map display area 110 on the defect confirmation screen 100. In this case, the map process processing unit 72, based on the wafer information data Dq1, at least produces the periphery of the wafer 90 and each die 91, thereby rendering the overall picture of the wafer 90.

Furthermore, the map process processing unit 72 may also render the intra-die inspection area in the map display area 110 based on the item information data Drs1 to Drs10 of the defect associated with each defect ID (defect ID data Drs) of one or a plurality of items of defect information data Dr1. In this way, the areas that have actually been inspected can be clarified, thereby making it easier to see the defect.

Thus, the map process processing unit 72 includes three map rendering modes concerning the rendering in the map display area 110 on the defect confirmation screen 100, as shown in FIG. 8, thereby enabling the display in the map-display area 110 to be made by three rendering methods associated with these map rendering modes.

FIG. 8 shows these modes of display in the map display area made by the map process processing unit.

In the present embodiment, there are the following three map rendering modes:
(1) A wafer overall rendering mode in which the entirety of the wafer 90 is displayed in the map display area 110
(2) A die rendering mode in which one or more dies 91 of the of wafer 90 are displayed in the map display area 110 in a superposed manner.
(3) A shot rendering mode in which one or more shots of the wafer 90 are displayed in a superposed manner.

The individual rendering modes can be switched by operating the GUI buttons 111 to 113 displayed on the defect confirmation screen 100 by the map process processing unit 72. So as to allow easy identification of the current rendering mode, the display color of the GUI button for the rendering mode that has been set based on the user operation through the input operating portion 53 is made different by the map process processing unit 72 from the color of the remaining GUI buttons 111 to 113 for the non-selected modes.

In the present embodiment, the wafer overall rendering mode (1) shown in FIG. 8 is associated with the "Wafer" button 111, the die rendering mode (2) is associated with the "Die" button 112, and the shot rendering mode (3) is associated with the "Shot" button 113.

These GUI buttons 111 to 113 may be shown in a combo-box display consisting of a combination of a rectangular region (text box) for the input of a map rendering mode and a map rendering mode selection list (list box). Alternatively, the GUI buttons may consist of radio buttons allowing the selection of any one of a plurality of selective map rendering modes.

In addition, the map rendering modes are each provided with three map operation modes. Upon selection of each map operation mode, the map process processing unit 72 carries out the following three operations concerning the map Mp rendered in the map display area 110 in a map rendering mode, as also shown in FIG. 8:
(1) An arbitrary defect selection operation by which an arbitrary defect on the map is selected.
(2) An arbitrary area selection operation by which a defect in an arbitrary area on the map is selected.
(3) An arbitrary area enlargement/reduction operation by which an arbitrary area on the map is enlarged or reduced in size.

The individual map operation modes can be switched by operating the GUI buttons 114 to 116 displayed on the defect confirmation screen 100 by the map process processing unit 72. So as to allow easy identification of the current map operation mode, the display color for any of the GUI buttons 114 to 116 for the map operation modes received and set in accordance with the user operation through the input operating portion 53 is made different by the map process processing unit 72 from the display color of the remaining GUI buttons for the other map operation modes.

In the present embodiment, the arbitrary defect selection operation (1) shown in FIG. 8 is associated with an arrow button 114 on the defect confirmation screen 100 shown in FIG. 4. Similarly, the arbitrary area selection operation (2) is associated with a rectangle-in-magnifying glass button 115, and the arbitrary area enlargement/reduction operation (3) is associated with a magnifying-glass button 116.

These GUI buttons 114 to 116 may be displayed in a combo-box consisting of a combination of a rectangular region (text box) for the input of a map operation mode and a map operation mode selection list (list box). Alternatively, the GUI buttons may consist of radio buttons enabling the turning-on of one map operation mode from a plurality of selective map operation modes.

By combining these three map rendering modes and three map operation modes, it becomes easier to see the connection between the image of each defect portion displayed in the map display area 110 and the item information data Drs1 to 10 shown in FIG. 6 associated with each detected-defect ID (i.e., for defect ID data Drs) of the defect information Dr1 in the inspection result data Dr.

For example, if it is desired to observe a plurality of defect portions concentrated at a certain location of the wafer 90 in one batch, the user may operate the Wafer button 111 using the mouse in the input operating portion 53 to select the wafer overall rendering mode (1) among the various map rendering modes on the defect confirmation screen 100, and then choose the arbitrary area selection operation (2) among the map operation modes by selecting the GUI buttons 111 to 116 shown in the map display area 110 on the defect confirmation screen 100, whereby the defects concentrated at one location can be easily selected.

Figure 9:
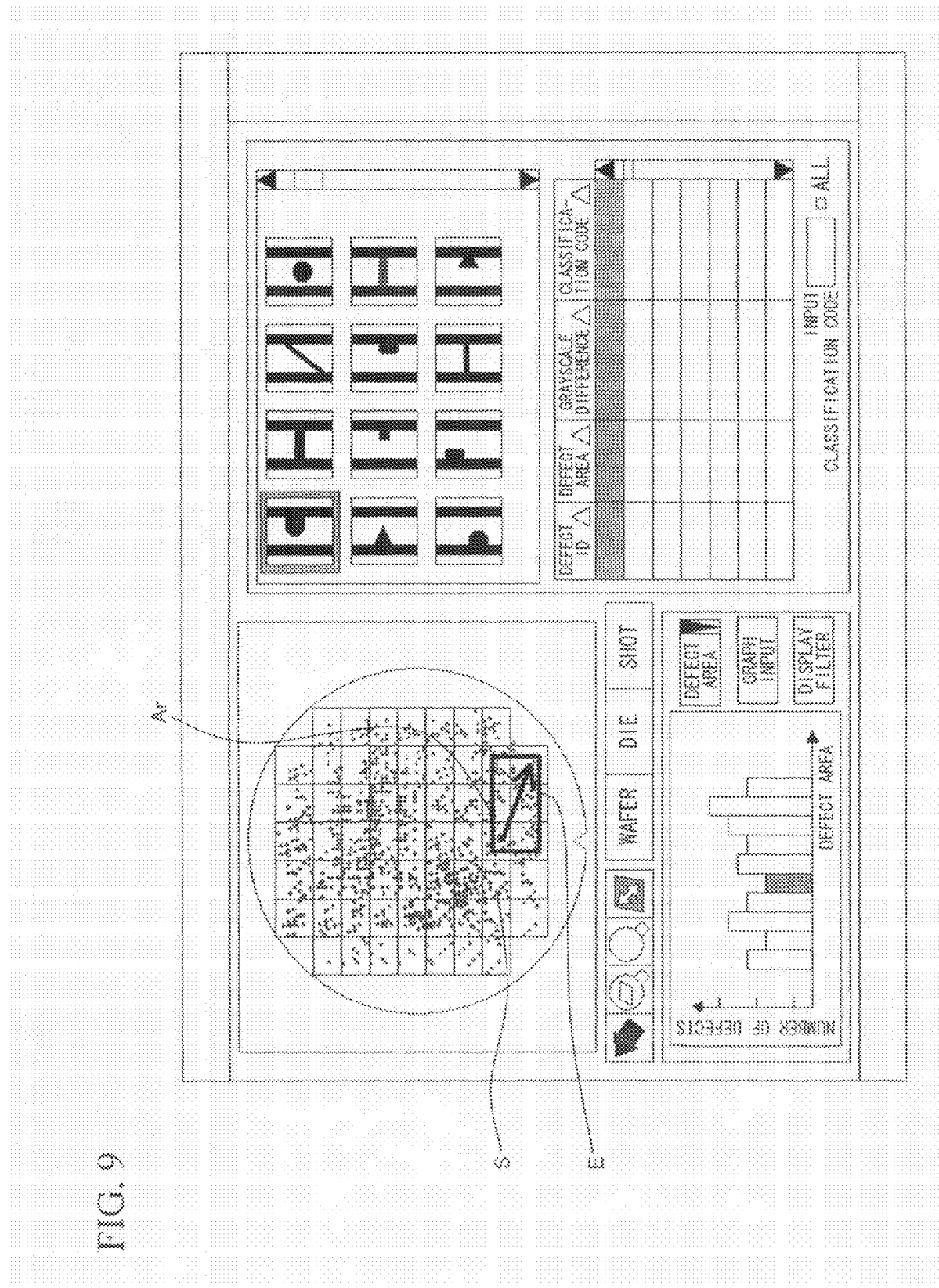
FIG. 9 shows a case where a defect in an arbitrary area of a map is selected by a map-drag startpoint/endpoint setting operation.
Figure 10:
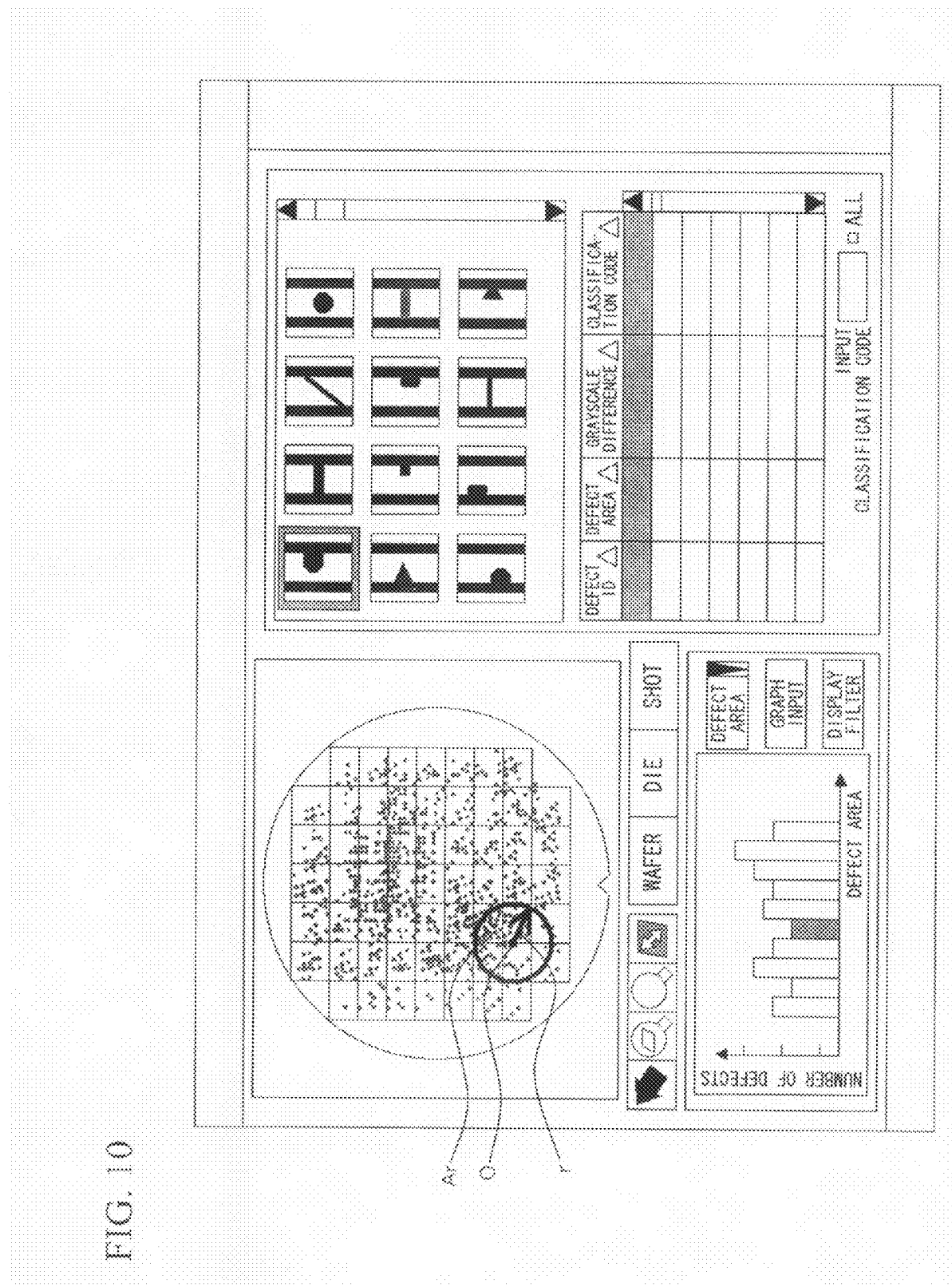
FIG. 10 shows a case where a defect in an arbitrary area of a map is selected by a map-drag circular region setting operation.
Figure 11:
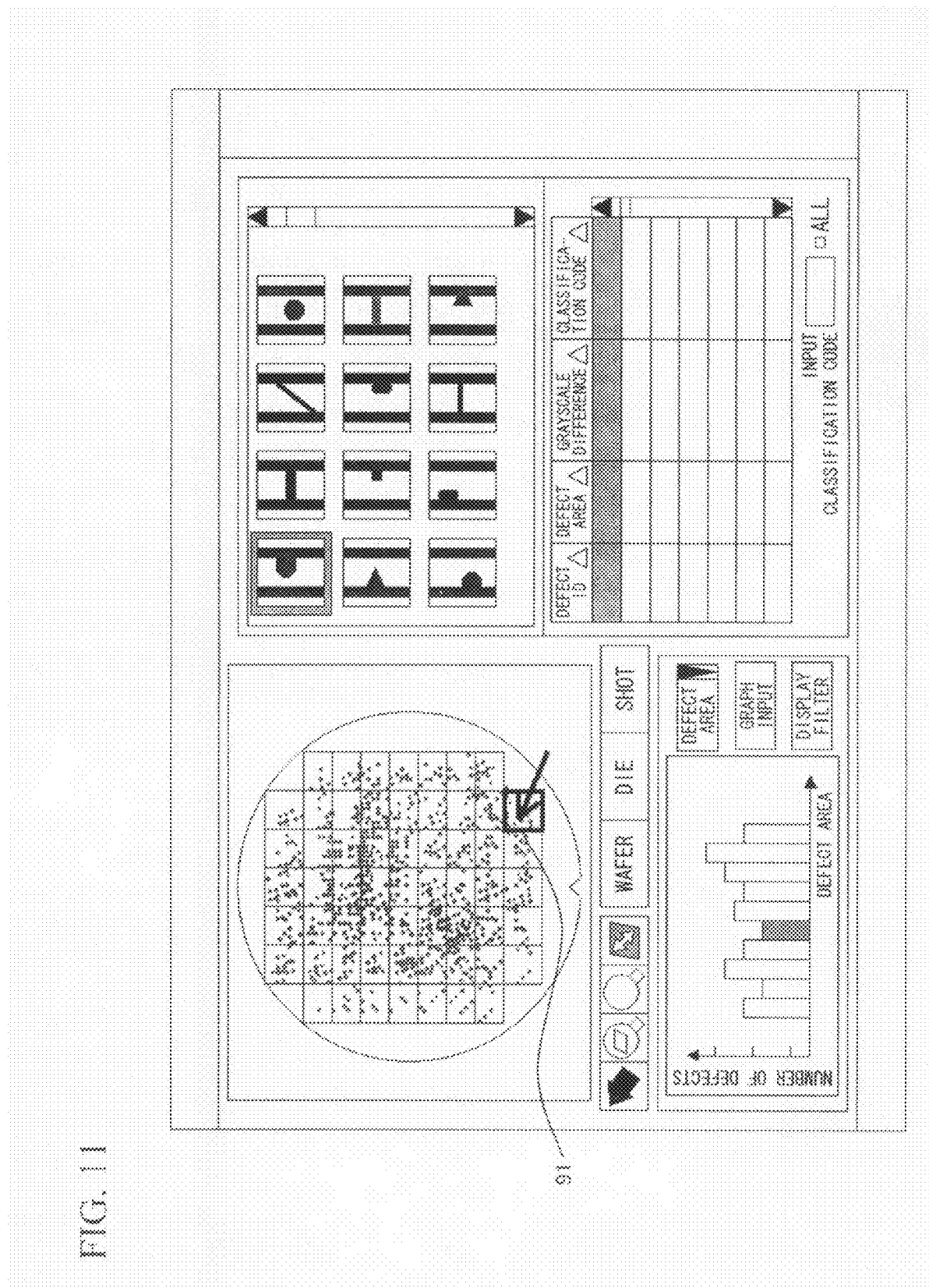
FIG. 11 shows a case where a defect in an arbitrary area of a map is selected by a map-clicking die-designating operation.

Further, in the present embodiment, for the selection of an arbitrary area during the aforementioned arbitrary area selection operation (2), the map process processing unit 72 is allowed to perform any of the three operating methods shown below, which are also shown in FIGS. 9, 10, and 11:
(1) A map-drag startpoint/endpoint setting operation involving the input of a start point and an end point.
(2) A map-drag circular region setting operation involving the input of a center point and a radius.
(3) A map-clicking die-designating operation involving the designation of a die.

FIG. 9 is a drawing for the description of the selection of defects in an arbitrary area in a map by the map-drag startpoint/endpoint setting operation.

As shown in FIG. 9, on the screen in the map display area 110 displayed in the wafer overall rendering mode, upon selection of a defect portion in an arbitrary area Ar on the map by the designation of an arbitrary start point S and end point E by dragging, the map process processing unit 72 supplies the defect ID data Drs for each location of the defects in the defect information data Dr1 in the inspection result data Dr associated with the defect portion in the selected area Ar. The map process processing unit 72 also supplies, if necessary, the item information data Drs1 to Drs10 associated with the defect ID data Drs to the message server portion 80. The message server portion 80 then supplies the defect ID data Drs supplied from the map process processing unit 72 and/or the item information data Drs1 to Drs10 associated with the defect ID data Drs to the other process processing unit 74, 76, and 78.

FIG. 10 shows a drawing for the description of how the defects in an arbitrary area on the map are selected by the map-drag circular region setting operation.

As show in FIG. 10, upon selection of defects in an arbitrary area on the map by designating an arbitrary point O and radius r by dragging, the map process processing unit 72 similarly supplies the defect ID data Drs and, if necessary, the item information data Drs1 to Drs10 corresponding to the defect portion within the selected circular area Ar to the message server portion 80. The message server portion 80 then supplies these to the other process processing units 74, 76, and 78.

FIG. 11 is a drawing for the description of how defects in an arbitrary die on the map are selected by the map-clicking die-designating operation.

As shown in FIG. 11, upon designation of an arbitrary die 91 on the map by clicking, the map process processing unit 72 similarly supplies the defect ID data Drs corresponding to the defect portion within the selected die 91 and/or the item information data Drs1 to Drs10 to the message server portion 80. The message server portion 80 then supplies these to the other process processing units 74, 76, and 78.

Thus, the map process processing unit 72, in addition to its function as a map display control unit for generating a defect portion map for display control, is provided with the function of a defect portion confirmation-region setting unit for setting an arbitrary region Ar on the map where confirmation of the defect portion is desired to be made.

In the following, the screen of the image display area 120 generated by the image process processing unit 74 on the defect confirmation screen 100 is described.

The image process processing unit 74, upon reception of defect ID data Drs and the like from the message server portion 80 following the supply of the defect ID data Drs and/or the item information data Drs1 to Drs10 from the map process processing unit 72 to the message server portion 80, causes individual images 121 of defect portions located within the selected arbitrary region Ar to be displayed in the image display area 120 on a defect portion basis, as shown in FIG. 4. The image process processing unit 74 displays an individual image 121 of at least one defect portion in the image display area 120. The image process processing unit 74 also stores the correspondence between the defect ID data for the individual images 121 of the defect portions that are currently on display in the image display area 120 and their display positions on the image display area 120 on an as-needed basis.

The size of each individual image 121 can be designated arbitrarily in terms of pixel size, for example, by a predetermined operation of the input operating portion 53. The image process processing unit 74 generates a display screen in the image display area 120 where any desired number of individual images 121 are displayed, in accordance with their designated size and the size of the image display area 120.

The total number of the individual images 121 caused to be displayed in the image display area 120 by the image process processing unit 74 depends on the map rendering mode for the map display area 110 notified by the map process processing unit 72, and on the number of items of defect ID data Drs in the arbitrary area Ar that is specified by the selection operation situation in the map operation mode. The total number varies greatly, ranging from one to several hundreds of thousands. Therefore, the image process processing unit 74, upon operation of a toolbar 122 provided in the image display area 120, changes the individual images 121 that are displayed in the image display area 120 by scrolling the individual images 121 displayed on the image display area 120, for example. The operation of the screen of the image display area 120 upon such change is not limited to the use of the toolbar 122; it may be based on a tabulation format, for example.

The individual images 121 of the defect portions caused to be displayed by the image process processing unit 74 do not necessarily need to be those individual images 121 that have already been stored in the storage unit 56. Specifically, the images may be those images that are now being inspected after having been fed to the image storage units 46 and 47 for defect determination by the determination unit 49. Furthermore, an image of the same location that has been re-acquired after inspection may be displayed.

Upon selection by the user of a desired individual image 121 by clicking on the mouse or the like of the input operating portion 53 from among the individual images 121 displayed in the image display area 120, the image process processing unit 74, based on the correspondence between the defect ID data of the individual image 121 now on display in the image display area 120 and the position of the defect portion in the image display area 120, identifies the defect ID data Drs for the selected individual image 121, and then supplies the defect ID data Drs for the defect portion corresponding to the selected individual image 121 and, as necessary, its item information data Drs1 to Drs10, to the message server portion 80. The message server portion 80 supplies the defect ID data Drs supplied from the image process processing unit 74 and the item information data Drs1 to Drs10 corresponding to the defect ID data Drs to the other process processing unit 72, 76, and 78.

If the user desires to select a plurality of individual images 121 from among the individual images 121 displayed in the image display area 120, the user can do so by, for example, dragging the mouse of the input operating portion 53 to the desired individual images 121 and clicking it while operating the Shift button and Ctrl button on the keyboard of the same input operating portion 53.

Thus, the image process processing unit 74, in addition to its function as the defect portion display control unit for generating the individual images of the defect portions for display control, is also provided with the function as a confirmation defect portion setting unit for setting a defect portion in which confirmation is desired to be made.

The defect ID data selected by the user as described above is supplied from the Drs message server portion 80 to the map process processing unit 72 by the image process processing unit 74. The map process processing unit 72, on the map Mp displayed (rendered) on the map display area 110, emphasizes the defect portion corresponding to the defect ID data Drs by highlighting, for example. Thus, the map process processing unit 72 is also equipped with a guidance notification unit for the defect portion designated by the image process processing unit 74 as the confirmation defect portion setting unit.

In the following, the screen of the list display area 130 on the defect confirmation screen 100 generated by the list process processing unit 76 is described.

The list process processing unit 76 includes the following functions:

(1) A defect information ∅list display function; and
(2) An function for adding information to a defect portion.

First, the defect information list display function of the list process processing unit 76 is described.

Upon reception of the defect ID data Drs and the like of the defect portion from the message server portion 80 based on the supply of the defect ID data Drs corresponding to the defect portion in the area Ar selected and, if necessary, the item information data Drs1 to Drs10 corresponding to the defect ID data Drs, from the map process processing unit 72 to the message server portion 80, the list process processing unit 76 generates a defect information list 131 based on the data supplied from the message server portion 80 and displays it in the list display area 130 using its list display function, as shown in FIG. 4.

In this process, the list process processing unit 76 may have items desired to be displayed on the defect information list 131 selected from the item information data Drs1 to Drs10 of the defect ID data Drs and stored in advance by a predetermined operation of the input operating portion 53. In this case, the list process processing unit 76 can generate the defect information list 131 based on the settings of the thus displayed items and then displays it in the list display area 130.

Upon reception by the list process processing unit 76 of the defect ID data Drs and the like of the defect portion from the message server portion 80, which is based on the supply of the defect ID data Drs for the defect portion corresponding to the selected individual image 121 from the image process processing unit 74 to the message server portion 80, and, if necessary, the supply of the item information data Drs1 to Drs10 corresponding to the defect ID data Drs, the list process processing unit 76 emphasizes the display of the defect ID data Drs in the supplied defect information list 131 by highlighting, changing its display color from the color used for the display of the other defect ID data Drs portions, or by drawing a navigating line, for example. In this way, the user can more easily recognize the defect ID data Drs portion of the individual image 121 that has been newly selected by the image process processing unit 74 in contrast to the other defect ID data Drs portions of the defect information list 131.

In this way, in the case where the defect ID data Drs supplied from the message server portion 80 is the defect ID data Drs that has been supplied from the image process processing unit 74 to the message server portion 80, the user can easily identify the defect ID data Drs corresponding to the defect portion designated by the image process processing unit 74 functioning as the confirmation defect portion setting unit, even on the defect information list 131 displayed in the list display area 130.

When the defect ID data Drs supplied from the message server portion 80 is the is the data supplied from the map process processing unit 72, the total number of defect portions (items of defect ID data Drs) displayed in the list display area 130 by the list process processing unit 76 varies widely from one to several hundreds of thousands. Thus, in this case, the list process processing unit 76, upon operation of the toolbar 132 provided in the list display area 130, changes the defect ID data Drs portions displayed in the list display area 130 by scrolling the list portion displayed in the list display area 130, for example. The screen operation in the list display area 130 for such change is not limited to the use of the toolbar 132; it may be based on a tabulation format, for example.

The user can designate a desired defect portion on the defect information list 131 on the screen of the defect information list 131 in the list display area 130 by clicking the mouse of the input operating portion 53, for example. For this purpose, the list process processing unit 76 stores the correspondence between the defect ID data Drs portion for the defect portion that is currently on display in the list display area 130 and the display position in the list display area 130 on an as-needed basis.

If the user desires to select a plurality of list portions for desired defect ID data Drs from the defect information list 131 displayed in the list display area 130, the user can do so by, for example, similarly dragging the mouse of the same input operating portion 53 to the list portions of the defect ID data Drs and clicking the mouse in combination with the operations of the Shift button and the Ctrl button on the keyboard of the same input operating portion 53.

If the user has selected one of the item names displayed in the defect information list 131, such as defect ID, defect area, grayscale difference, and classification code, for example, and designated the order of the items by operating the input operating portion 53, the list process processing unit 76, based on such designation, sorts the detailed information concerning each of the defect portion displayed in the list in the designated order of the selected item, such as in the descending or ascending order of the data values, for example, thereby rearranging the defect information list.

The list process processing unit 76, when creating the defect information list 131, adds a selection check box in addition to the items of the item information data Drs1 to Drs10 of each defect portion corresponding to each defect ID data Drs that have been selected for display. In this case, the list process processing unit 76 removes the linkage between only the data about the defect portion that has been checked in the selection check box list by the user on the defect information list 131 displayed in the display area 130 by operating the input operating portion 53, and the data about the defect portions that are not checked.

The screen of the list display area 130 shown in FIG. 4 is an example in which the selection check box is provided in the form of a selection check box 133 for one-batch selection. In the illustrated example, when setting a new classification code or allocating a clustering number in the defect information list 131 in one operation, for example, the user can check the one-batch selection check box 133 on the screen and cause the list process processing unit 76 to set one classification code or clustering number for all of the defect portions in the defect information list 131 by simply entering the settings for the classification code or a clustering number just once via the input operating portion 53. In the case of the aforementioned sorting function, checking the box activates a select-all or a nullify-all function while deactivating the sorting function for the other items.

In the following, the function of the list process processing unit 76 to add information to a defect portion is described.

The list process processing unit 76 is provided with the function of allocating at least one item of information to the defect portion (defect ID data Drs) selected by the user on the defect information list 131 by operating the input operating portion 53. Thus, the list process processing unit 76 is capable of adding an item of information to the selected defect portion in addition to the existing items in the defect information list 131.

In the case of the present embodiment, a classification code entry box 133 is provided on the screen of the list display area 130 shown in FIG. 4. With the use of this box, the user can allocate classification code data (manual classification code data) to the defect portions in the defect information list 131 individually or entirely, by manual input via the input operating portion 53 separately from the classification code data (automatic classification code data) Drs6 for the inspection result data Dr shown in FIG. 6. For such manual entry of a manual classification code through the input operating portion 53, the user can designate the desired defect portions in the defect information list 131 by clicking the mouse of the input operating portion 53, for example, with the aforementioned selection check box 133 not checked, and then manually enter a classification code in the classification code entry box 134 via the keyboard of the input operating portion 53. In this case, the list process processing unit 76, based on the input operation via the input operating portion 53, gives guidance by emphasizing the display of the defect portions in the defect information list 131 to which a new manual classification code is to be allocated, and then add the manual classification code entered in the selection check box 133 to the relevant defect portions in the defect information list 131. Thereafter, the list process processing unit 76 moves the emphasis-guidance to the defect portion on the defect information list 131 next to the defect portion to which the manual classification code has been allocated, and renders the defect portion in a classification code entry state. On the other hand, when allocating the same manual classification code to all of the defect portions in the defect information list 131, the selection check box 133 is checked and then the classification code is entered in the classification code entry box 133. Other examples of information given in the defect information list 131 other than the above-described classification code include a clustering number and marking information for marking an important defect portion in contrast to the other, unimportant defect portions.

Upon designation of a desired defect portion on the defect information list 131 in the list display area 130 by the clicking of the mouse of input operating portion 53 as described above, the list process processing unit 76 supplies the defect ID data Drs of the designated defect portion on the defect information list 131 and, if necessary, its item information data Drs1 to Drs10 and the like, to the message server portion 80. The message server portion 80 then supplies the defect ID data Drs and the item information data Drs1 to Drs10 and the like corresponding to the defect ID data Drs to the other process processing units 72, 74, and 78.

Thus, the list process processing unit 76, in addition to the above function, is provided with the function of a confirmation defect portion setting unit for setting a defect portion for which confirmation is desired.

To the map process processing unit 72, the defect ID data Drs selected by the user in the list process processing unit 76 is supplied from the message server portion 80. The map process processing unit 72, on the map Mp being displayed in its map display area 110, emphasizes the defect portion corresponding to the defect ID data Drs by highlighting, for example.

Similarly, from the message server portion 80, the defect ID data Drs selected by the user in the list process processing unit 76 as described above is supplied to the image process processing unit 74. The image process processing unit 74 then emphasizes the individual image 121 of the defect portion corresponding to the defect ID data Drs in its image display area 120 by highlighting, for example.

Alternatively, the apparatus may be configured such that the earlier-described image process processing unit 74 and the above list process processing unit 76, in addition to the defect ID data Drs selected by the user, also supplies the defect ID data Drs of the individual image 121 of the defect portion currently on display in the image display area 120, and the defect ID data Drs of the defect portion currently on display in the list display area 130, to the message server portion 80, wherein the message server portion 80 supplies the defect ID data Drs of the defect portion on the defect information list 131 displayed in the image display area 120 to the image process processing unit 74 and the defect ID data Drs of the defect portion displayed in the list display area 130 to the list process processing unit 76. In this way, the image process processing unit 74 and the list process processing unit 76 can have their respective toolbars 122 and 132 linked with each other so that the individual image 121 of the defect portion displayed in the image display area 120 and the defect information list 131 displayed in the list display area 130 can be synchronized with each other.

In the following, the screen of the list display area 130 on the defect confirmation screen 100 generated by the graph process processing unit 78 is described.

The graph process processing unit 78 has the following functions:

(1) A function for displaying defect information in a graph; and (2) A display filter function for the defect displayed in the map Mp.

First, the defect information graph display function of the graph process processing unit 78 is described.

Upon reception of the defect ID data Drs and the like of the defect portion from the message server portion 80 based on the supply of the defect ID data Drs corresponding to the defect portion in the area Ar selected in the map process processing unit 72 and, if necessary, the item information data Drs1 to Drs10 corresponding to the defect ID data Drs, the graph process processing unit 78, using its defect information graph display function, and based on the defect area data Drs3, classification code Drs6, grayscale difference data Drs9, ... corresponding to the notified defect ID data Drs as shown in FIG. 6, generates a defect analysis graph 141 that indicates the relationship between a designated information item in these items and the number of defects (namely, the number of items of the defect ID data Drs), and then displays the graph in the graph display area 140. In the case shown in FIG. 4, the defect analysis graph 141 that is generated and displayed in the graph display area 140 shows the defect area as the designated information item in the horizontal axis and the number of the displayed defects, or the number of the defect IDs, per defect area value, shown in the vertical axis.

The graph process processing unit 78 is capable of displaying the defect analysis graph 141 in either a bar graph or a line graph bar, depending on the user selection based on a predetermined operation of the input operating portion 53.

The graph process processing unit 78 also shows a GUI combo-box 142 in the graph display area 140 for the designation and change of the information item among the item information data Drs1 to Drs10 that is to be displayed in the defect analysis graph 141. The user can designate or change the information item on the screen of the graph display area 140 using the input operating portion 53. In the combo-box 142, the user can select an arbitrary information item from among the entire item information data Drs1 to Drs10. The manner of designation of an information item on the screen of the graph display area 140 is not limited to the use of the combo-box 142; it may be based on radio buttons or pre-set buttons, for example.

Upon change in the designation of an information item in the graph display area 140 through the operation of the combo-box 142, the graph process processing unit 78 generates a defect analysis graph 141 showing the data values of the designation-altered information item in the horizontal axis and the number of displayed defects per information item data value in the vertical axis, thereby updating the contents of the defect analysis graph 141 displayed in the graph display area 140.

Upon reception of the defect ID data Drs and the like of the defect portion from the message server portion 80 based on the supply from the image process processing unit 74 or the list process processing unit 76 to the message server portion 80 of the defect ID data Drs and the like corresponding to the selected individual image 121 or defect portion, the graph process processing unit 78, by referring to the defect analysis graph 14 currently on display in the graph display area 140, emphasizes the display contents of a portion of the graph that includes the count of the defects corresponding to the defect ID data Drs, by highlighting, by using a color different from the color of the other bars, or by drawing a navigating line, for example.

In this way, the user can easily recognize the location of the individual image 121 he or she selected from among the individual images 121 displayed in the image display area 120, and the location of the defect portion selected by the user from the defect information list 131 displayed in the list display area 130, in the defect analysis graph 141 displayed in the graph display area 140.

In the present embodiment, the "magnifying glass" GUI button 116 shown in the map display area 110 for the enlargement or reduction in size of an arbitrary area in the map Mp rendered in the map display area 110 can also be used for an arbitrary area in the defect analysis graph 141 displayed in the graph display area 140. In this case, the graph process processing unit 78, upon designation of an arbitrary portion in the defect analysis graph 141 by a designating operation of the magnifying glass button 116, enlarges or reduces the size of the thus designated arbitrary portion alone in the graph display area 140. The display (graph information) of the designated arbitrary portion of the defect analysis graph 141 enlarged or reduced in size in the graph display area 140 is caused by the graph process processing unit 78 to maintain the display of the designated arbitrary portion in the defect analysis graph 141 until the magnifying glass button 116 is operated for designation purpose.

Regarding such arbitrary designated portion, the graph process processing unit 78 supplies the defect ID data Drs of the defect portion counted in the arbitrary designated portion and, as necessary, the item information data Drs1 to Drs10 corresponding to the defect ID data Drs, to the message server portion 80. The message server portion 80 supplies the defect ID data Drs and the item information data Drs1 to Drs 10 corresponding to the defect ID data Drs to the other process processing units 72, 74, and 76. Upon reception of the supply of the defect ID data Drs and the like of the defect portion included in the arbitrary designated portion in the defect analysis graph 141 from the message server portion 80, the map process processing unit 72 emphasizes the defect portion corresponding to the defect ID data Drs on the map Mp in the map display area 110, by highlighting, for example. Similarly, the image process processing unit 74 emphasizes the individual image 121 of the defect portion corresponding to the defect ID data Drs in the image display area 120 by highlighting or the like. The list process processing unit 76 emphasizes the display contents of the defect portion corresponding to the defect ID data Drs in the list display area 130 in the defect analysis graph 141 by highlighting or the like.

In this way, the user can monitor the details of the defect portion corresponding to a characteristic portion of the graph selected by the user on the defect analysis graph 141 displayed in the graph display area 140, on the map Mp in the map display area 110, on the individual image 121 in the image display area 120, and on the defect information list 131 in the list display area 130.

In the following, the function of the graph process processing unit 78 for filtering the display of the defect displayed on the map Mp is described.

As shown in FIG. 4, the graph process processing unit 78 causes GUI buttons consisting of a graph input button 144 and a display filter button 143 to be displayed in the graph display area 140 along with the defect analysis graph 141. These buttons are used for setting, on the defect analysis graph 141 displayed in the graph display area 140, filtering information for regulating the defect portion displayed in the map display area 110 by the map process processing unit 72.

Figure 12:
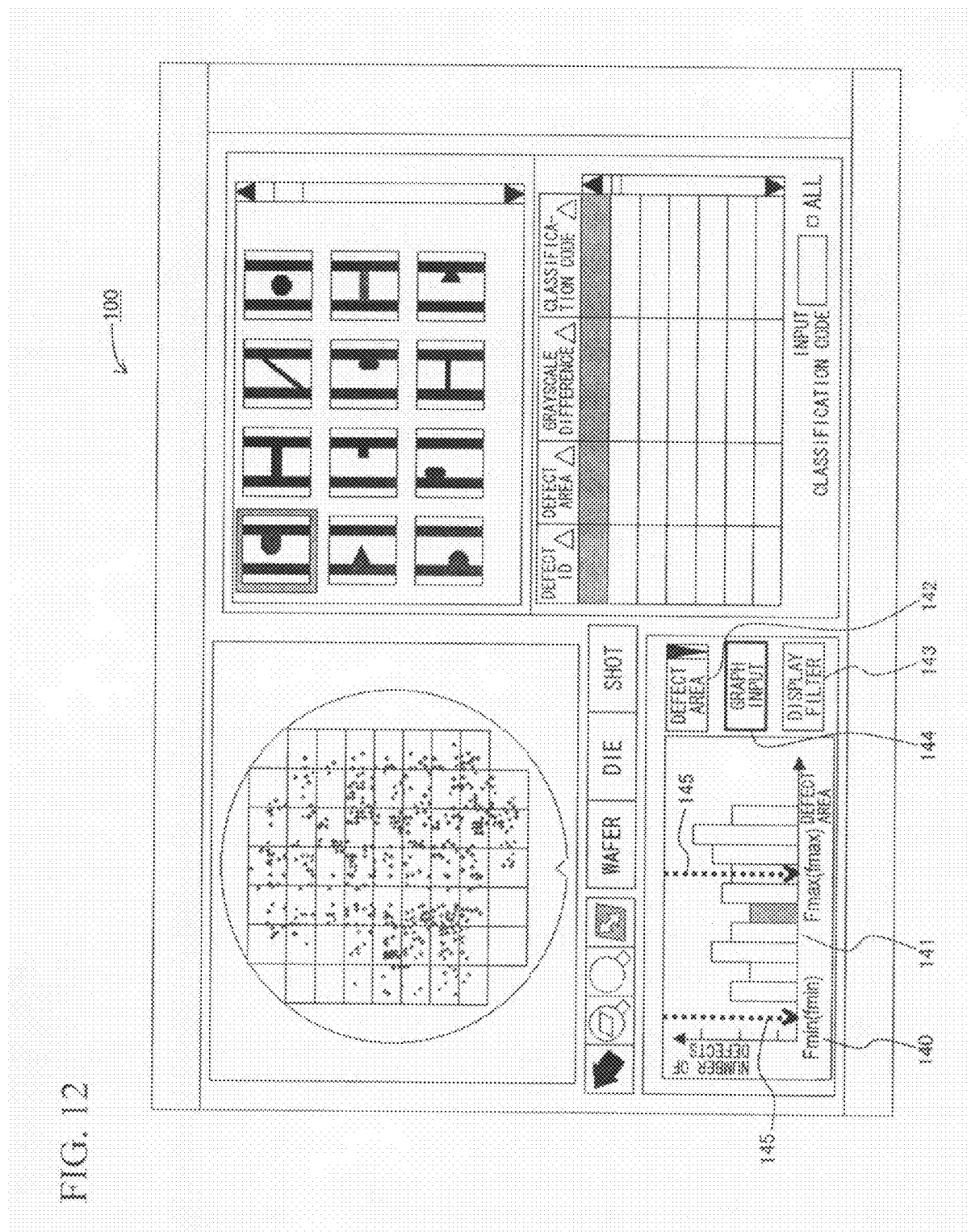
FIG. 12 shows how filtering information for regulating the defect portion displayed in the map display area is set.

FIG. 12 is a drawing for the description of how the filtering information for regulating the defect portion displayed in the map display area is set.

In the present embodiment, as the user clicks the graph input button 144 GUI-displayed in the graph display area 140 using the mouse of the input operating portion 53, the graph process processing unit 78 detects this and enables the user to set the information item (which is the areal information in the example of FIG. 12) selected on the defect analysis graph 141 currently on display in the graph display area 140, using the display on the defect analysis graph 141. Thus, the graph process processing unit 78 also functions as a filtering information setting unit for setting the information for filtering the defect displayed in the map display area 110. In this filtering information set state in the graph process processing unit 78, the user can operate the mouse of the input operating portion 53 for dragging or clicking so as to set an upper limit value Fmax and a lower limit value Fmin of the filtering information on the defect analysis graph 141. In the present embodiment, the upper limit value Fmax and the lower limit value Fmin of the filtering information are set in the following manner. For example, when setting the upper limit value Fmax, the mouse pointer is dragged to an item coordinate position fmax on the defect analysis graph 141 that corresponds to a desired upper limit value Fmax of an information item (which is the areal information in the example of FIG. 12) on the defect analysis graph 141, and then the mouse is right-clicked. When setting the lower limit value Fmin, the mouse pointer is dragged to an item coordinate position fmin on the defect analysis graph 141 that corresponds to a desired lower limit value Fmin of the information item, and then the mouse is left-clicked.

The graph process processing unit 78 acquires the coordinates position of the mouse pointer on the screen of the graph display area 140 upon right- or left-clicking the mouse on the defect analysis graph 141, converts the coordinates position of the mouse pointer into a coordinates position on the item coordinates (which is a coordinate position on the coordinates axes of the areal information in the example of FIG. 12) f, sets an upper limit value Fmax or a lower limit value Fmin of filtering information based on such coordinates, and then displays the thus set upper limit value Fmax or the lower limit value Fmin of the filtering information in the form of boundary lines 145 on the defect analysis graph 141 in the graph display area 140, as shown in FIG. 12.

The graph process processing unit 78, whenever it sets the upper limit value Fmax or the lower limit value Fmin of filtering information in the filtering information set state based on the operation of the mouse of the input operating portion 53, supplies the defect ID data Drs of the defect portion in the information item data range defined by the upper limit value Fmax and/or the lower limit value Fmi of the filtering information that has been set and, as necessary, the item information data Drs1 to Drs10 corresponding to the defect ID data Drs, to the message server portion 80, together with the upper limit value Fmax or the lower limit value Fmin of the filtering information. The message server portion 80 then supplies the upper limit value Fmax or the lower limit value Fmin of the filtering information that have been set by the graph process processing unit 78 in the filtering information set state, and the defect ID data Drs and the like supplied from the graph process processing unit 78 in the filtering information set state, to the other process processing units 72, 74, and 76.

Upon reception of the upper limit value Fmax or the lower limit value Fmin of the filtering information from the message server portion 80 that have been set by the graph process processing unit 78 in the filtering information set state, and the defect ID data Drs and the like from the graph process processing unit 78 in the filtering information set state, the map process processing unit 72 deletes the display of the defect ID data Drs from the map Mp in the map display area 110 other than the supplied defect ID data Drs, and displays a map Mp of the defect portion adapted to the range of information item data (Fmin to Fmax) defined by the upper limit value Fmax and/or the lower limit value Fmin of the filtering information newly set by the graph process processing unit 78 in the filtering information- set state. Similarly, the image process processing unit 74 displays in the image display area 120 an individual image 121 of the defect portion included in the information item data range defined by the upper limit value Fmax and/or the lower limit value Fmi of the filtering information that has been newly set by the graph process processing unit 78 in the filtering information set state. The list process processing unit 76 displays in the list display area 130 a list of the defect portions in the information item data range (Fmin to Fmax) defined by the upper limit value Fmax and/or the lower limit value Fmi of the filtering information newly set by the graph process processing unit 78 in the filtering information set state in the list display area 130.

Thus, in the present embodiment, the number of defect portions on the map Mp displayed in the map display area 110, the number of individual images 121 of the defect portions displayed in the image display area 120, and the number of the defect portions displayed in the list display area 130 all vary and either increase or decrease, depending on the number of the defect portions included in the information item data range (Fmin to Fmax) defined on the defect analysis graph 141 of the information item displayed in the graph display area 140 by the graph process processing unit 78 in the filtering information set state.

The filtering information set state of the graph process processing unit 78 is released by a re-operation of the graph input button 144.

The implemented filter condition can be confirmed by a "Display filter" button. The filter conditions entered via the graph can be confirmed by the Display filter button, as shown in FIG. 13. This function allows the filter conditions visually entered on the graph to be edited or implemented again.

FIG. 13 shows a drawing for the description of a screen for confirming the filtering information set state of the graph process processing unit.

On the filtering information set state confirmation screen 200 of the present embodiment, a filter condition that is difficult to enter via the graph can be displayed and implemented, so that a more effective display filter can be implemented.

In the foregoing description of the linkage of the display contents of the map display area 110, the image display area 120, the list display area 130, and the graph display area 140 on the defect confirmation screen 100, examples were used in which in the map display area 110 of the defect confirmation screen 100, the wafer overall rendering mode is set such that the entire wafer 90 in the above-described map rendering mode shown in FIG. 8 is displayed in the map display area 110. The same description also applies to the case where, in the map rendering mode shown in FIG. 8, the die rendering mode is selected by which one or more dies 91 of the wafer 90 are displayed in the map display area 110 in a superposed manner, or the shot rendering mode is selected whereby one or more shots of the wafer 90 are displayed in a superposed manner.

For example, in cases where the die rendering mode or the shot rendering mode is selected, too, a defect distribution map Mp can be created on the basis of the inspection result data Dr shown in FIG. 6 and by focusing on the intra-die coordinates or the intra-shot coordinates as the defect coordinates data Drs1 in the defect information data Dr1 of the inspection result data Dr.

Figure 14:
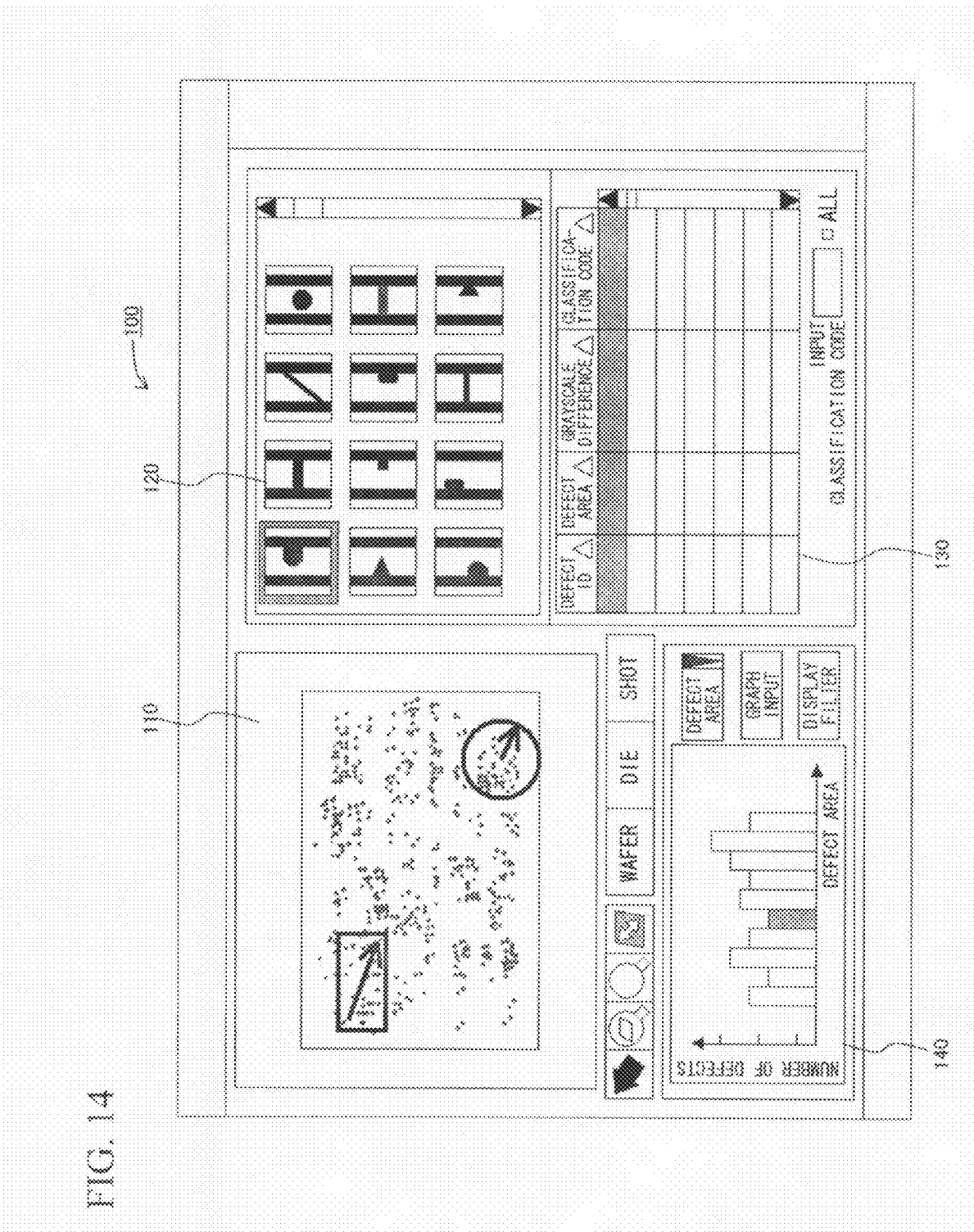
FIG. 14 shows a defect confirmation screen in a case where a die rendering mode is set as the map rendering mode.

FIG. 14 shows the defect confirmation screen in a case where the die rendering mode is set as the map rendering mode.

Figure 15:
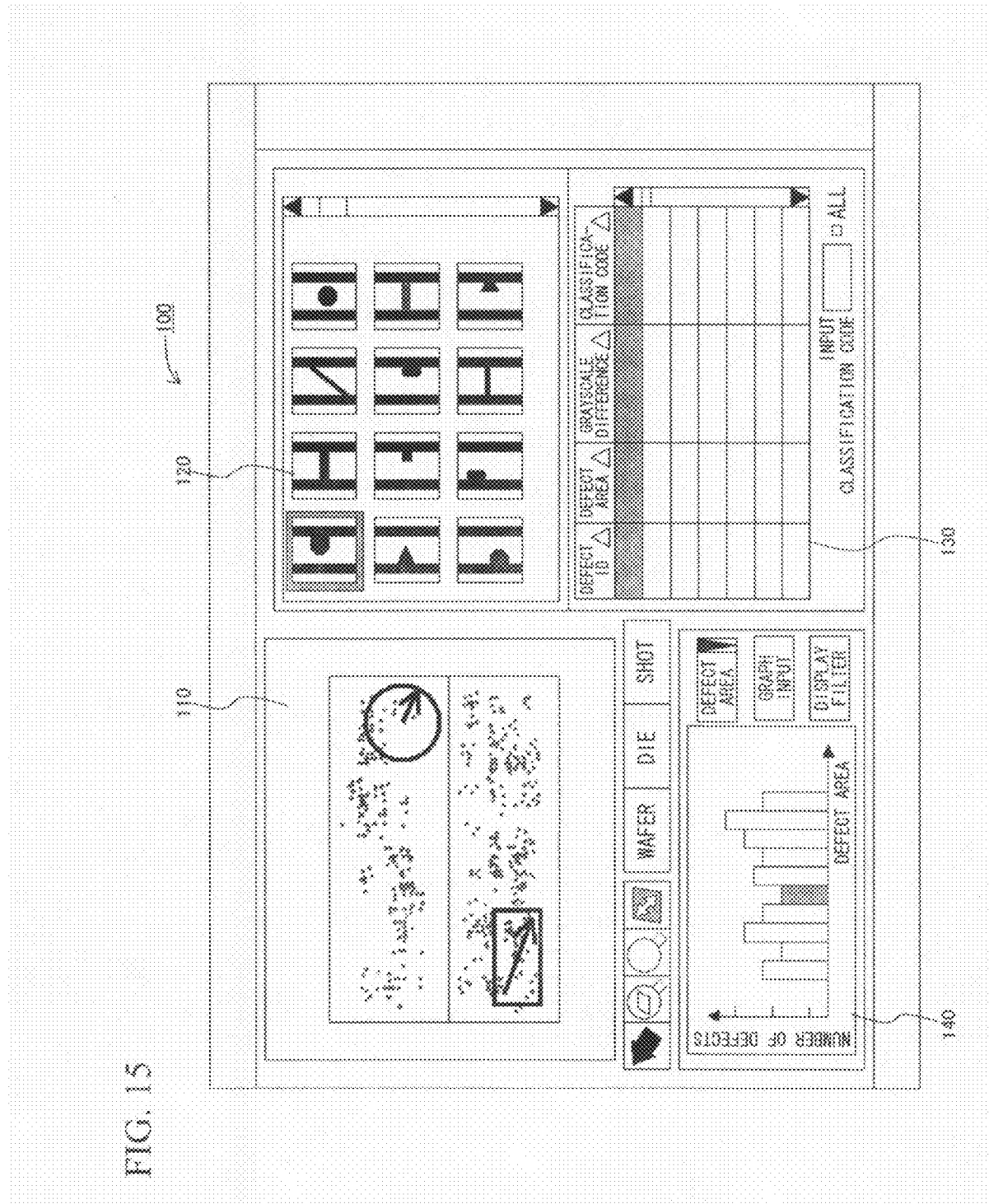
FIG. 15 shows a defect confirmation screen in a case where a shot rendering mode is set as the map rendering mode.

FIG. 15 shows the defect confirmation screen in a case where the shot rendering mode is set as the map rendering mode.

Thus, the manner of display differs between dies or shots in the defect confirmation screen 100 of FIG. 14 according to the die rendering mode or in the defect confirmation screen 100 of FIG. 15 according to the shot rendering mode in the map display area 110, so that defects that appear in the same die or shot can be easily detected.

In the cases of both the defect confirmation screen 100 by the die rendering mode and the defect confirmation screen 100 by the shot rendering mode, the linkage of the display contents in the map display area 110, the image display area 120, the list display area 130, and the graph display area 140 is the same as in the aforementioned case where the wafer overall rendering mode is set. Thus, by using the die rendering mode or the shot rendering mode, it becomes possible to easily detect a defect that appears in the same die 91 or the same shot.

While the above-described function is effective for defect confirmation after the normal inspection, it is more effective on the defect confirmation screen 100 during the creation of a recipe.

During the creation of the recipe Rp shown in FIG. 5, the following three functions can be registered in the recipe information as automatic implementation processes after inspection:

(1) A classification code providing function based on defect information.
(2) A clustering function based on defect coordinates.
(3) Automatic filtering function.

The first function, i.e., the automatic classification code providing function based on the defect information Dr1 of the inspection result data Dr shown in FIG. 6, is a function for creating an area (to be hereafter referred to as a classification area) in the defect classification code entered by the user for enabling maximum classification, and for registering such area in the recipe Rp.

Figure 16:
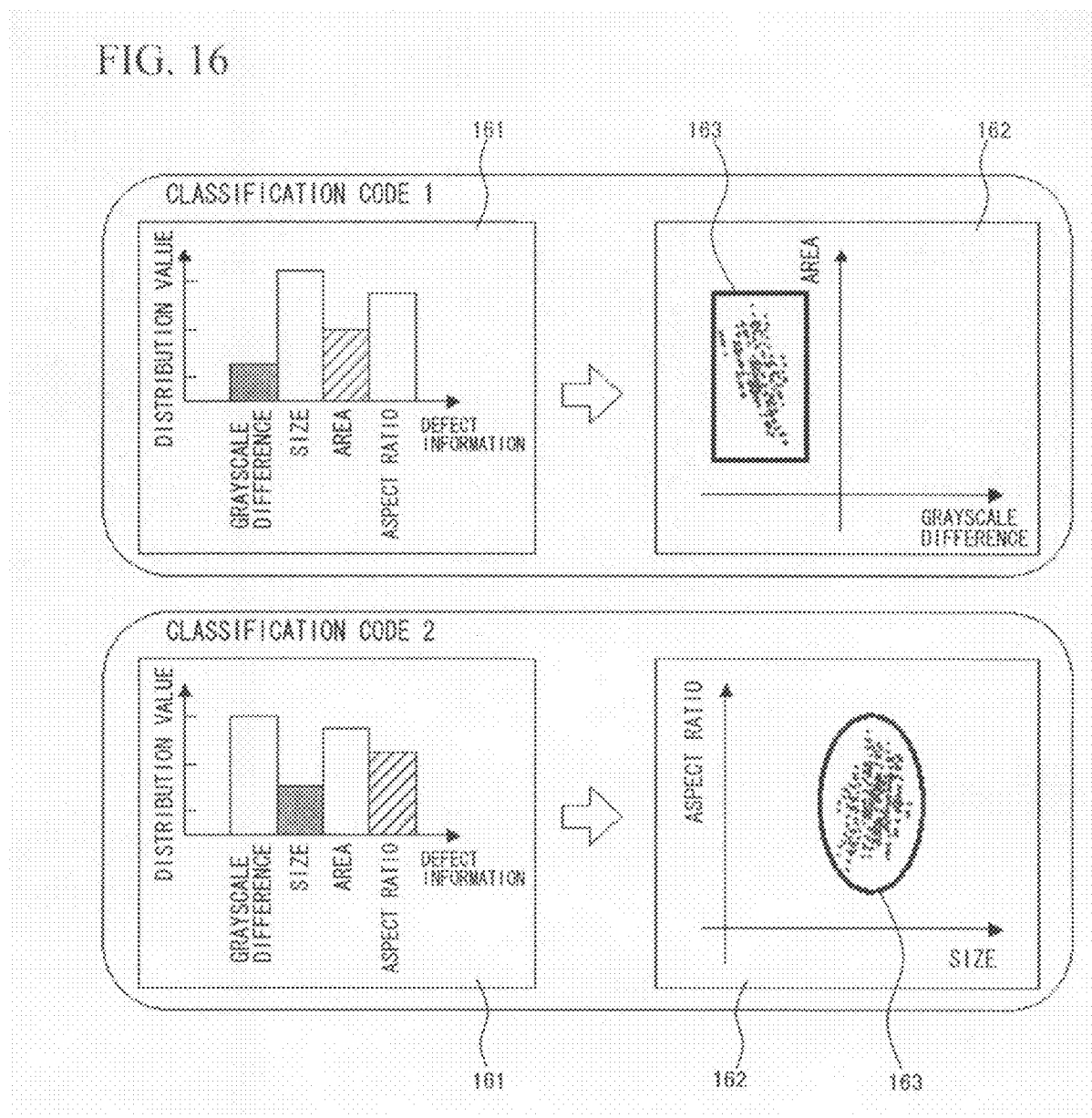
FIG. 16 shows classification methods based on defect information.

FIG. 16 shows a drawing for the description of a classification method based on defect information.

For example, when the defect portion corresponding to the classification code 1 of the defect entered by the user includes the grayscale difference data Drs8, the defect size data Drs4, the defect area data Drs3, and the aspect ratio (vertical/horizontal ratio) data Drs5 of characteristic defect information Dr1, as indicated by a graph 161 shown in FIG. 16 showing the distribution values of each item of defect information, the individual items of the contents of the individual image 121 of each defect portion allocated to the classification code 1, namely, the grayscale difference data Drs 8, the defect size data Drs 4, the defect area data Drs 3, and the aspect ratio data Drs 5, are tallied by the control unit 6 of the inspection apparatus 1 in the defect information Dr1 of the inspection result data Dr, and the distribution value of each item is calculated. A graph 161 showing the calculated results is displayed on the screen of the monitor 50.

As shown in the graph 161 of FIG. 16, the control unit 6 of the inspection apparatus 1 automatically selects one or more items in the order of increasing value of the calculated distribution value of the items. In the present embodiment, two items, namely, the grayscale difference data Drs 8 and the defect area data Drs 3, are selected and classified two dimensionally.

Then, a rectangular or elliptical classification region (classification area) 163 is designated on a grayscale difference—defect portion map 162 such that the classification code 1 that has been set is attached to those defect portions of the selected defect portions that exceed the designated classification percentage. The control unit 6 of the inspection apparatus 1 then displays the grayscale difference—defect portion map 162 on which the designated classification area is shown on the same screen of the monitor 50, together with the graph 161.

The designated classification percentage is 3σ in default and can be changed as a parameter.

As to the classification code 2, too, similar processes are carried out so as to create a classification area 163.

When classification codes overlap, one classification code is determined according to preset individual classification code priorities.

The user can confirm the classification area 163 graphically on the graph and can also make changes easily.

The classification area 163 can be more dynamically changed by dragging the line designating the classification area 163 on the grayscale difference—defect portion map 162 displayed on the screen of the monitor 50 as shown in FIG. 16.

As to the priority of the classification code, the user can set for each recipe Rp, and the user can also choose a rectangle, for example, for the classification area 163 although it is elliptical in default.

By adding "intra-die coordinates" and "intra-shot coordinates" to the elements of which the axes of the classification area 163 are composed, it becomes possible to easily recognize a reticle defect that is detected on the identical coordinates on another die and on the identical coordinates of another shot.

The second function, namely the defect clustering function is a function for registering a clustering condition entered by the user in the recipe Rp shown in FIG. 5.

The number of defects of minimum elements of a clustering group entered by the user and the distance between minimum defects are registered in the recipe Rp as a clustering condition.

The clustering condition can be designated also by entering the values of the minimum number of elements (minimum number of defects of which a cluster is composed) and the element-to-element distance (distance between defects).

The third function, namely, the filtering function, is a function for registering filtering information entered by the user using the filter function of FIG. 15 in the recipe Rp.

Filter items that cannot be entered via the map Mp are entered via a designation dialog.

For example, such items include an arbitrary number of filters from arbitrary defect ID, and the inspection method (cell comparison detection defect, die comparison detection defect, mixed comparison detection defect).

In order to clearly distinguish from a filter temporarily used for defect classification, the control unit 6 of the inspection apparatus 1 requests that the user perform operations with registration in the recipe Rp in mind.

In the present embodiment, a dialog box is displayed for determining whether or not the filter that has been used after defect confirmation and that is currently in effect should be registered in the recipe Rp.

Figure 17:
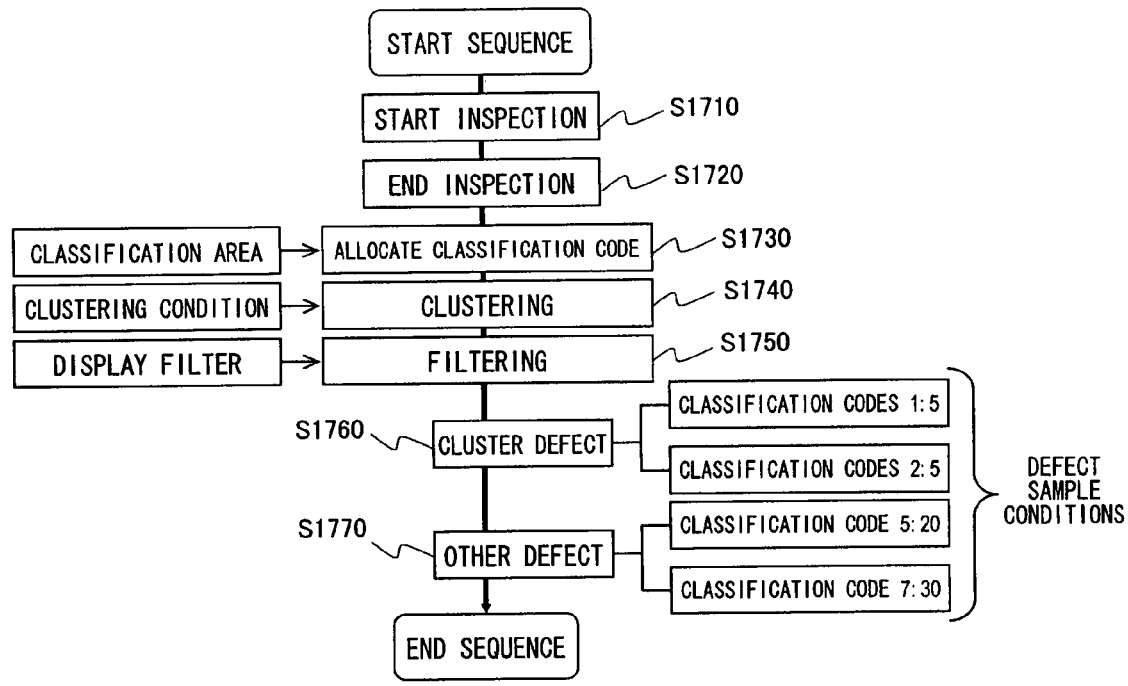
FIG. 17 shows a flowchart of the process concerning a defect image sample condition.

These three processes are performed after inspection, and then a defect image sample condition of a hierarchical structure is set in the recipe as shown in FIG. 17. In this way, a very efficient defect confirmation can be made after inspection.

FIG. 17 shows a flowchart of a defect image sample condition process.

As shown in FIG. 17, this defect image sample condition of a hierarchical structure enables the designation of "cluster defect"—"classification code", and also "classification code"—"cluster defect".

Such defect image sample condition having a hierarchical structure can be used not only as an image sample condition but also for defect confirmation.

Thus, the condition can be registered in the recipe Rp and simultaneously in an external review condition file, and it can be easily loaded as a review condition upon loading of another recipe Rp.

Figure 18:
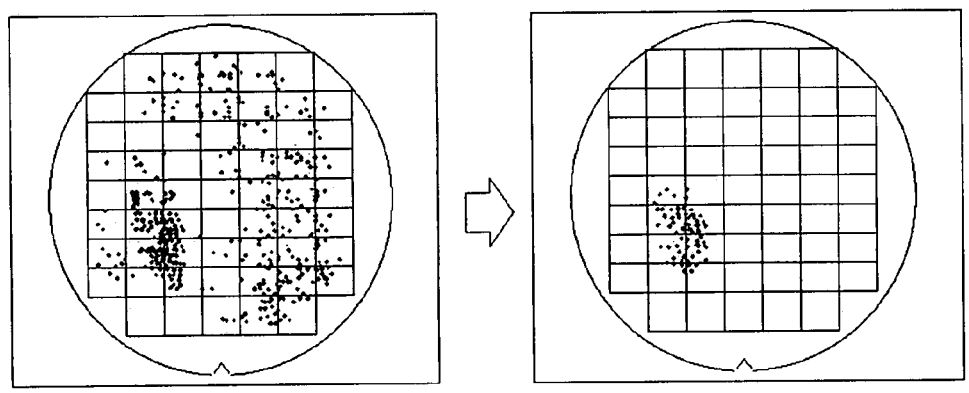
FIG. 18 shows a defect distribution map after inspection before the application of the present invention.
Figure 19:
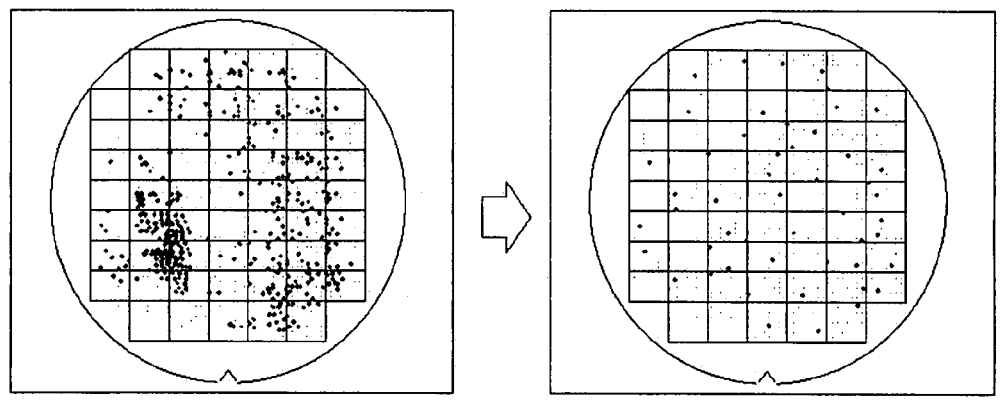
FIG. 19 shows a defect distribution map after inspection after the application of the present invention.

FIGS. 18 and 19 show defect distribution maps of the results of inspection based on a recipe Rp prior to the application of the invention, and the results of inspection after the application of the invention.

As will be seen from the drawings, in the defect distribution map prior to the application of the invention, many concentrated defect portions are sampled and as a result an effective defect confirmation cannot be made. In contrast, in the defect distribution map after the application of the invention, the wafer as a whole is substantially uniformly sampled, enabling a more effective defect confirmation.

The foregoing has been the description of the circuit pattern inspection apparatus and method according to the present embodiment. The apparatus and method can be modified in various ways.

Figure 20:
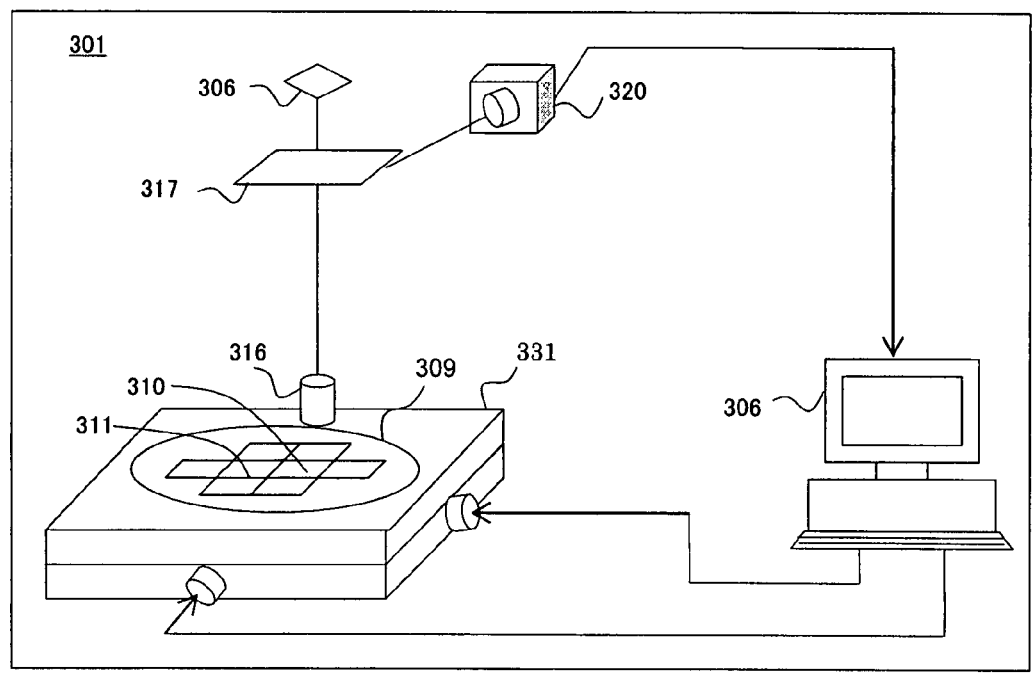
FIG. 20 shows a block diagram of the overall configuration of a wafer exterior inspection apparatus according to another embodiment of the invention.

For example, they can be applied to a wafer exterior inspection apparatus 301 shown in FIG. 20 in which the light source employs light or laser light.

FIG. 20 shows a block diagram of the overall configuration of a wafer exterior inspection apparatus according to another embodiment of the invention.

An inspected wafer 309 is placed on an X-Y stage 331. On top of the inspected wafer 309, chips are regularly arranged and formed in a lattice. A control unit 306 moves the X-Y stage 331 by a distance that is an integer multiple of the chip pitch. The light source 306 emits light with which the inspected wafer 309 is irradiated. The light reflected by the inspected wafer 309 passes through an objective lens 316, has its optical path divided by a half mirror 317, and then detected by a CCD camera 320 as a two-dimensional image.

By moving the X-Y stage 331 by the chip pitch using the control unit 306, whereby images can be obtained at the identical point between an inspected chip 310 and a comparison chip 311.

The control unit 306, based on the grayscale difference at the identical point between inspected chip 310 and the comparison chip 311, determines that there is a defect at the inspected point of the inspected chip 310 if the difference is greater than a predetermined threshold value.

What is claimed is:

1. A circuit pattern inspection apparatus comprising:
   an irradiation means for irradiating the surface of a substrate on which a wafer circuit pattern is formed with either light, laser light, or a charged-particle beam;
   a detection means for detecting a signal produced by the substrate upon irradiation;
   an inspection image acquisition means for acquiring images of the wafer circuit pattern as inspection images by converting the signal detected by the detection means into images;
   a defect determination means for comparing the inspection images obtained by the inspection image acquisition means with a reference image different from the inspection images that are acquired from an identical circuit pattern so as to determine a defect portion produced on the circuit pattern from which the inspection images have been acquired;
   an analysis result display means for generating a defect confirmation screen on which the inspection images acquired by the inspection image acquisition means, an analysis image based on the inspection images, and another analysis image based on the result of defect determination made by the defect determination means are arranged;
   an input means for entering information on a defect confirmation screen generated by the analysis result display means in a dialog mode; and
   an image linkage means for changing, when an operation input has been made using the input means on either the analysis image based on the inspection images disposed or on the analysis image based on the result of determination that are arranged on the defect confirmation screen, the display contents of one analysis image are changed in a corresponding manner in operative linkage with the operation input made on the other analysis image via the input means.

2. The circuit pattern inspection apparatus according to claim 1, wherein the analysis result display means generates at least one analysis image based on the inspection image disposed on the defect confirmation screen using the input means, or based on the result of defect determination made by the defect determination means.

3. The circuit pattern inspection apparatus according to claim 1, wherein the input means comprises means for selecting an irradiation condition for the irradiation means via the defect confirmation screen.

4. The circuit pattern inspection apparatus according to claim 2, wherein the input means also functions as a recipe setting means for setting an irradiation condition for the irradiation means as recipe data, wherein the irradiation condition is selected on the defect confirmation screen.

5. A circuit pattern inspection method comprising the steps of:
   irradiating the surface of a substrate on which a wafer circuit pattern is formed with light, laser light, or a charged-particle beam;
   detecting a signal produced by the substrate upon irradiation;
   imaging the thus detected signal and acquiring images of the wafer circuit pattern as inspection image images;
   comparing the inspection images with a reference image that is separated from the inspection images and that is acquired from an identical circuit pattern; and
   determining a defect portion produced on the circuit pattern from which the inspection images have been acquired, based on the result of comparison,
   the method further comprising:
   an analysis result display step of generating a defect confirmation screen on which the inspection images, an analysis image based on the inspection images and an analysis image based on the result of defect determination are arranged;
   an input step of entering information on the defect confirmation screen generated in the analysis result display step in a dialog mode; and
   an image linkage step of changing, when an operation input has been made using the input means on either the analysis image based on the inspection images disposed or on the analysis image based on the result of determination that are arranged on the defect confirmation screen, the display contents of one analysis image are changed in a corresponding manner in operative linkage with the operation input made on the other analysis image via the input means.

* * * * *